United States Patent
Wright et al.

(10) Patent No.: US 7,223,849 B1
(45) Date of Patent: May 29, 2007

(54) OLIGONUCLEOTIDES FROM THE UNTRANSLATED REGIONS OF HOUSEKEEPING GENES AND METHODS OF USING SAME TO MODULATE CELL GROWTH

(75) Inventors: Jim A. Wright, Toronto (CA); Aiping H. Young, Toronto (CA)

(73) Assignee: Genesense Technologies Inc., Toronto, Ontario (CA)

( * ) Notice: Subject to any disclaimer, the term of this patent is extended or adjusted under 35 U.S.C. 154(b) by 0 days.

(21) Appl. No.: 09/214,386

(22) PCT Filed: Jun. 30, 1997

(86) PCT No.: PCT/CA97/00454

§ 371 (c)(1),
(2), (4) Date: May 21, 1999

(87) PCT Pub. No.: WO98/00532

PCT Pub. Date: Jan. 8, 1998

Related U.S. Application Data

(60) Provisional application No. 60/021,152, filed on Jul. 1, 1996.

(51) Int. Cl.
| | |
|---|---|
| C07H 21/04 | (2006.01) |
| A61K 31/70 | (2006.01) |
| C12N 15/00 | (2006.01) |
| C12Q 1/68 | (2006.01) |

(52) U.S. Cl. .......................... 536/23.1; 514/44; 435/6; 435/320.1

(58) Field of Classification Search .............. 435/91.1, 435/6, 91.31, 392.5; 536/23.1, 24.3, 24.5; 530/387.1; 514/44
See application file for complete search history.

(56) References Cited

U.S. PATENT DOCUMENTS

| | | | |
|---|---|---|---|
| 4,358,535 A * | 11/1982 | Falkow et al. | |
| 4,736,866 A | 4/1988 | Leder et al. | |
| 4,873,191 A | 10/1989 | Wagner et al. | |
| 5,175,383 A | 12/1992 | Leder et al. | |
| 5,175,384 A | 12/1992 | Krimpenfort et al. | |
| 5,175,385 A | 12/1992 | Wagner et al. | |
| 5,221,778 A | 6/1993 | Byrne et al. | |
| 5,225,347 A | 7/1993 | Goldberg et al. | |
| 5,288,846 A | 2/1994 | Quertermous et al. | |
| 5,298,422 A | 3/1994 | Schwartz et al. | |
| 5,347,075 A | 9/1994 | Sorge | |
| 5,360,735 A | 11/1994 | Weinshank et al. | |
| 5,387,742 A | 2/1995 | Cordell | |
| 5,464,764 A | 11/1995 | Capecchi et al. | |
| 5,487,992 A | 1/1996 | Capecchi et al. | |
| 5,601,818 A | 2/1997 | Freeman et al. | |
| 5,614,396 A | 3/1997 | Bradley et al. | |
| 5,998,383 A * | 12/1999 | Wright et al. | |
| 6,342,483 B1 * | 1/2002 | Holt et al. | 514/44 |

FOREIGN PATENT DOCUMENTS

| | | |
|---|---|---|
| EP | 0 383 190 A2 | 8/1990 |
| EP | 0 726 277 A2 | 8/1996 |
| WO | WO 93/14200 | 7/1993 |
| WO | WO 93/17125 | 9/1993 |
| WO | WO 94/06908 | 3/1994 |
| WO | WO 94/28123 | 5/1994 |
| WO | 94/21661 | 9/1994 |
| WO | WO 94/23049 | 10/1994 |
| WO | 95/02069 | 1/1995 |
| WO | 98/00532 | 1/1998 |

OTHER PUBLICATIONS

Anderson, Nature 392/Supp. p. 25-30, Apr. 1998.*
Branch, TIBS 23 p. 45-50, Feb. 1998.*
Flanagan et al., Nature Biotech. 17:48-52, Jan. 1999.*
Crystal, Science vol. 270, p. 404-410, Oct. 1995.*
Pavloff et al, DNA Sequence, vol. 2, pp. 227-234, 1992.*
Amara et al, NAR vol. 23, No. 9, p. 1461-1467, 1995.*
Chandra Sekharappa et al. vol. 12, No. 1, p. 173-180, Jan. 1986.*
Chen et al., EMBO vol. 12 No. 10. pp. 3977-3986, 1993.*
Voss et al., J. Biol. Chem, vol. 266 No. 21, pp. 13706-13711, 1991.*
Tsa et al., J. Biol. Chem., vol. 266 No. 34, pp. 23053-23059, 1991.*
Braidotti et al., J. Biol. Chem., vol. 268 No. 2, pp. 1109-1117, 1993.*
Hilfiker et al., J. Biol. Chem., vol. 268 No. 26, pp. 19717-19725, 1993.*
Michael J. McCluskie et al., Route and Method of Delivery of DNA Vaccine Influence Immune Responses In Mice and Non-Human Primates; Molecular Medicine, vol. 5, No. 5 May 1999 pp. 287-300.*
J. Gomez-Navarro et al., Gene Therapy for Cancer; European Journal of Cancer, vol. 35, No. 6 pp. 867-885, 1999.*
Agrawal et al., Molecular Medinine Today, 2000, vol. 6, p. 72-81.*
Opalinska et al. Nature Reviews Drug Discovery, 2002, vol. 1, p. 503-514.*
Jen et al. Stem Cells 2000, vol. 18, p. 307-319.*
Agrawal, S., et al. "Antisense therapeutics" *Current Opinion in Chemical Biology*, 2:519-528, (1998).
Schabet, M., et al., "Animal models of leptomeningeal metastasis" *Journal of Neuro-Oncology*, 38:199-205, (1998).
Thelander, L., et al., "Isolation and Characterization of Expressible CDNA Clones Encoding the M1 and M2 Subunits of Mouse Ribonucleotide Reductase" *Molecular and Cellular Biology*, vol. 6, No. 10, pp. 3433-3442, (Oct. 1986).
Takeda, E., et al., "Role of Ribonucleotide Reductase In Expression Of The Neoplastic Program" *Life Sciences*, vol. 28, pp. 1007-1014 (1981).

(Continued)

Primary Examiner—James Schultz
Assistant Examiner—Tracy Vivlemore
(74) Attorney, Agent, or Firm—The Nath Law Group; Gary M. Nath; Lee C. Heiman

(57) ABSTRACT

The invention relates to oligonucleotides from the untranslated regions of housekeeping genes, and methods and compositions for modulating cell growth using same. Specifically it relates to the use of the untranslated regions (UTR) from housekeeping genes specifically the R1 and R2 components of ribonucleotide reductase UTR, for inhibiting tumor cell growth.

52 Claims, 2 Drawing Sheets

OTHER PUBLICATIONS

Kijima, H., et al., "Therapeutic Applications of Ribozymes" *Pharmac. Ther.*, vol. 68, No. 2, pp. 247-267, (1995) XP 000612090.

Amara, F.M., et al, Altered Regulation of Message Stability and Tumor Promoter-responsive *cis-trans* Interactions of Ribonucleotide Reductase R1 and R2 Messenger RNAs in Hydroxyurea-resistant Cells, Cancer Research, 55:4503-4506, 1995.

Amara, F.M., et al., A novel transforming growth factor-beta responsive cytoplasmic trans-acting factor binds selectively to the 3'-untranslated region of mammalian ribonucleotide reductase R2 mRNA: role in message stability, Nucleic Acids Research, 21:4803-4809, 1993.

Altschul, S.F., et al., Basic Local Alignment Search Tool, 403-410, 1990.

Chen, F.Y., et al., Mammalian ribonucleotide reductase R1 mRNA Stability under normal and phorbol ester stimulating conditions: involvement of a *cis-trans* interaction at the 3' untranslated region, The EMBO Journal, 12(10):3977-3986, 1993.

Cregg, J.M., et al., Recent Advances in the Expression of Foreign Genes in *Pichia pastoris*, Bio/Technology, 11:905-910, 1993.

Fan, H., et al., Suppression of Malignancy by the 3' Untranslated Regions of Ribonucleotide Reductase R1 and R2 Messenger RNAs, Cancer Research, 56:4366-4369, 1996.

Greene, L.A., et al., Establishment of a noradrenergic clonal line of rat adrenal pheochromocytoma cells which respond to nerve growth factor, Proc. Natl. Acad. Sci. USA, 73(7):2424-2428, 1976.

Gubler U. and Hoffman, B.J., A simple and very efficient method for generating cDNA libraries, Gene, 45:263-269, 1983.

Parker, N.J., et al., Human M1 subunit of ribonucleotide reductase: cDNA sequence and expression in stimulated lymphocytes, Nucleic Acids Research, 19(13):3741, 1991.

Pavloff, N., et al., Sequence analysis of the large and small subunits of human ribonucleotide reductase, DNA Sequence, 2:227-234, 1992.

EMBL/GenBank/DDBJ Databases, Accession number No. aa452273, Unpublished, created Jun. 11, 1997, Hillier, et al., "WachU-Merck Est Project 1997", XP002048834.

EMBL/GenBank/DDBJ Databases, Accession number No. g07100, Unpublished, created Jun. 15, 1995, Hudson, et al., "The Whitehead Institute/MIT Center for Genome Research; Physically mapped ESTs", XP002048239.

Agrawal et al., 1991. Pharmacokinetics, biodistribution, and stability of oligodeoxynucleotide phosphorothioates in mice. Proc. Natl. Acad. Sci. USA 88:7595-7599.

Agrawal, 1996. Antisense oligonucleotides: towards clinical trials, TIBTECH, 14:376.

Akhter et al, 1991. Interactions of antisense DNA oligonucleotide analogs with phospholipid membranes (liposomes). Nuc. Res. 19:5551-5559.

Amara et al., 1994. Phorbol ester modulation of a novel cytoplasmic protein binding activity at the 3'-untranslated region of mammalian ribonucleotide reductase R2 mRNA and role in message stability. J. Biol. Chem. 269:6709-7071.

Amara et al., 1995B. Defining a novel *cis* element in the 3'-untranslated region of mammalian ribonucleotide reductase component R2 mRNA: Role in transforming growth factor-$b_1$ induced mRNA stabilization. Nucleic Acids Res. 23:1461-1467.

Amara et al. 1996. Defining a novel *cis*-element in the 3'-untranslated region of mammalian ribonucleotide reductase component R2 mRNA: *cis-trans* interactions and message stability. J. Biol. Chem. 271:20126-20131.

Ashihara and Baserga, 1979. Cell Synchronization. Methods Enzymol. 58:248-262.

Blaesse, 1997. Gene Therapy for Cancer. Scientific American 276(6):111-115.

Björklund et al., 1993. Structure and promoter characterization of the gene encoding the large subunit (R1 Protein) of mouse ribonucleotide reductase. Proc. Natl. Acad. Sci. USA 90:11322-11326.

Burke and Olson, "Preparation of Clone Libraries in Yeast Artificial-Chromosome Vectors" in *Methods in Enzymology*, vol. 194, "Guide to Yeast Genetics and Molecular Biology", eds. C. Guthrie and G. Fink, Academic Press, Inc., Chap. 17, pp. 251-270 (1991).

Caceres and Kosik, 1990. Inhibition of neurite polarity by tau antisense oligonucleotides in primary cerebellar neurons. Nature, 343:461.

Capecchi, "Altering the genome by homologous recombination" *Science* 244:1288-1292 (1989).

Caras, 1985. Cloned Mouse Ribonucleotide Reductase Subunit M1 cDNA Reveals Amino Acids Sequence Homology with *Escherichia coli* and Herpesvirus Ribonucleotide Reductases. Biol Chem. 260:7015-7022.

Chan et al., 1993. Phosphorylation of ribonucleotide reductase R2 protein: *in vivo* and *in vitro* evidence of a role for $pd4^{cdc2}$ and CDK2 protein kinases. Biochemistry 32:12835-12840.

Chen et al., 1993. Mammalian ribonucleotide reductase R1 mRNA stability under normal and phorbol ester stimulating conditions: involvement of *cis-trans* interaction at the 3'-untranslated region. EMBO J., 12:3977-3986.

Chen et al., 1994A. Regulation of mammalian ribonucleotide reductase R1 mRNA stability is mediated by a ribonucleotide reductase R1 mRNA 3'-untranslated region *cis-trans* interaction through a protein kinase C-controlled pathway. Biochem. J. 302:125-132.

Chen et al., 1994B. Defining a novel ribonucleotide reductase R1 mRNA *cis* element that binds to an unique cytoplasmic *trans*-acting protein. Nucleic Acids Res., 22:4796-4797.

Choy et al., 1988. Molecular mecahnisms of drug resistance involving ribonucleotide reductase: hydroxyurea resistance in a series of clonally related mouse cell lines selected in the presence of increasing drug concentrations. Cancer Res. 48:2029-2035.

Cifone and Fidler, 1981. Increased metastatic potential is associated with increasing genetic instability of clones isolated from murine neoplasms. Proc. Natl. Acad. Sci. USA 78:6949-6952.

Crooke, 1995. Progress in antisense therapeutics, Hematol. Pathol. 2:59.

Damen et al., 1989. Generation of metastatic variants in populations of mutator and amplificator mutants. J. Natl. Cancer Inst. 81:628-631.

Davis et al., 1994. Purification, Characterization, and Localization of Subunit Interaction Area of Recombinant Mouse Ribonucleotide Reductase R1 Subunit. Biol. Chem. 269:23171-23176.

Davies et al., "Targeted alterations in yeast artificial chromosomes for inter-species gene transfer", *Nucleic Acids Research*, vol. 20, No. 11, pp. 2693-2698 (1992).

Dickinson et al., "High frequency gene targeting using insertional vectors", *Human Molecular Genetics*, vol. 2, No. 8, pp. 1299-1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Eckstein 1985. Nucleoside Phosphorothioates. Ann. Rev. Biochem. 54:367-402.

Egan, et al., 1987A. Expression of H-*ras* Correlates with Metastatic Potential: Evidence for Direct Regulation of the Metastatic Phenotype in 10T1/2 and NIH 3T3 Cells. Mol. Cell. Biol. 7:830-837.

Egan et al., 1987B. Transformation by oncogenes encoding protein kinases induces the metastatic phenotype. Science 238:202-205.

Eriksson et al., 1984. Cell cycle-dependnet regulation of mammalian ribonucleotide reductase. The S phase-correlated increase in subunit M2 is regulated by *de novo* protein synthesis. J. Biol. Chem. 259:11695-11700.

Fan et al., 1996A. Ribonucleotide reductase R2 component is a novel malignancy determinant that cooperates with activated oncogenes to determine transformation and malignant potential. Proc. Natl. Acad. Sci. USA 93:14036-14040.

Fan et al., 1996B. A link between ferritin gene expression and ribonucleotide reductase R2 protein, as demonstrated by retroviral vector mediated stable expression of R2 cDNA. FEBS Lett. 382:145-148.

Fan et al., 1996C. Cloning of a gene from *Chlamydia trachomatis* that complements thymidylate synthase-deficient *Escherichia coli*.

*In:* Abstracts of the 94th General Meeting of the American Society for Microbiology, p. 134. [*n/a—will mail in].

Farrell and Lukens, 1995. Naturally occurring antisense transcripts are present in chick embryo chondrocytes simultaneously with the down-regulation of the a1 (I) collagen gene. J. Biol. Chem. 270:3400-3408.

Filatov et al., 1996. Induction of the mouse ribonucleotide reductase R1 and R2 genes in response to DNA damage by UV light. J. Biol. Chem. 271:23698-23704.

Ford et al., 1997. The poly (A) tail inhibits the assembly of a 3'-to 5' exonuclease in an in vitro RNA stability system. Mol. Cell. Biol. 17:398-406.

Galileo et al., 1991. Retrovirally Introduced Antisense Integrin RNA Inhibits Neuroblast Migration In Vivo. Neuron 9:1117-31, 1992).

Gewirtz, 1993. Oligodeoxynucleotide-based therapeutics for human leukemias, Stem Cells Dayt. 11:96.

Gilboa et al., 1986. Transfer and expression of cloned genes using retroviral vectors. BioTechniques 4(6):504-512.

Gordon, 1989. Transgenic Animals. Intl. Rev. Cytol. 115:171-129.

Hake and Richer, 1997. Translation regulation of maternal mRNA. Biochim. Biophys. Acta 1332:M31-M38.

Hampel and Tritz, 1989. RNA Catalytic Properties of the Minimum (-) sTRSV Sequence. Biochemistry 28:4929-4933.

Hanania, et al 1995. Recent advances in the application of gene therapy to human disease. Am. J. Med. 99:537.

Huston et al, 1991 "Protein engineering of single-chain Fv analogs and fusion proteins" in Methods in Enzymology (JJ Langone, ed.; Academic Press, New York, NY) 203:46-88.

Huang and Wright, 1994. Fibroblast growth factor mediated alterations in drug resistance, and evidence of gene amplification. Oncogene 9:491-499.

Huang et al., 1995A. Drug resistance and gene amplification potential regulated by transforming growth factor $b_1$ gene expression. Cancer Res. 55:1758-1762.

Huang et al., 1995B. Multiple effects on drug sensitivity, genome stability and malignant potential by combinations of H-*as*, *c-myc* and mutant p53 gene overexpression. Int. J. Oncol. 7:57-63.

Hurta, et al., 1991. Early induction of ribonucleotide reductase gene expression by transforming growth factor $b_1$ in malignant H-*ras* transformed cell lines. J. Biol. Chem. 266:24097-24100.

Hurta and Wright, 1992. Alterations in the activity and regulation of mammalian ribonucleotide reductase by chlorambucil, a DNA damaging agent. J. Biol. Chem. 267:7066-7071.

Hurta and Wright, 1995. Malignant transformation by H-*ras* results in aberrant regulation of ribonucleotide reductase gene expression by transforming growth factor-$b_1$ J. Cell. Biochem. 57:543-556.

Huxley et al., "The human HPRT gene on a yeast artificial chromosome is functional when transferred to mouse cells by cell fusion", *Genomics*, 9:742-750 (1991).

Iyer et al. 1990. The Automated Synthesis of Sulfur-Containing Oligodeoxyribonucleotides Using 3*H*-1,2-Benzodithiol-3-one 1,1-Dioxide as a Sulfur-Transfer Reagent, J. Org. Chem. 55:4693-4699.

Jakobovits et al., "Germ-line transmission and expression of a human-derived yeast artificial chromosome", *Nature*, vol. 362, pp. 255-261 (1993).

Jensen et al., 1994. Identification of genes expressed in premalignant breast disease by microscopy-directed cloning. Proc. Natl. Acad. Sci, USA. 91:9257-9261.

Johnson and Bird, 1991 Construction of single-chain Fvb derivatives of monoclonal antibodies and their production in *Escherichia coli* in Methods in Enzymology (JJ Langone, ed.; Academic Press, New York, NY) 203:88-99.

Kimelman and Kirschner, 1989. An antisense mRNA directs the covalent modification of the transcript encoding fibroblast growth factor in *Xenopus* oocytes. Cell 59:687-696.

Klausner and Hartford, 1989. *Cis-trans* models for post-transcriptional gene regulation. Science 246:870-872.

Lamb et al., "Introduction and expression of the 400 kilobase *precursor amyloid protein* gene in transgenic mice", *Nature Genetics*, vol. 5, pp. 22-29 (1993).

Lavitrano et al, 1989. Cell 57:717-723 [*n/a—will mail in].

Lee et al., 1993. The C. elegans Heterochronic Gene *lin*-4 encodes small RNAs with Antisense Complementarity to *lin*-14. Cell 75:843-854.

Lefebvre-D'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In *Antisense Therapeutics*, A. Cohen and S. Smicek, eds (Plenum Press, New York).

Lewis et al., 1978. Assay of ribonucleotide reduction in nucleotide-permeable hamster cells. J. Cell Physiol. 94:287-298.

Loke et al, 1989. Characterization of oligonucleotide transport into living cells. PNAS USA 86:3474-3478.

Mann et al., 1988. Ribonucleotide reductase M1 subunit in cellular proliferation, quiescence, and differentiation. J. Caner Res. 48:5151-5156.

Marzluff and Pandey, 1988. Multiple regulatory steps control histone mRNA concentrations. Trends Biochem. Sci. 13:49-52.

McClarty et al., 1990. Increased ferritin gene expression is associated with increased ribonucleotide reductase gene expression and the establishment of hydroxyurea resistance in mammalian cells. J. Biol. Chem. 265:7539-7547.

Miller et al., 1993. User of retroviral vectors for gene transfer and expression. Meth. Enzymol. 217:581-599.

Mernaugh and Mernaugh, 1995 "An overview of phage-displayed recombinant antibodies" in Molecular Methods In Plant Pathology (RP Singh and US Singh, eds.; CRC Press Inc., Boca Raton, FL) pp. 359-365.

Morrison, 1991. Suppression of basic fibroblast growth factor expression by antisense oligonucleotides inhibits the growth of transformed human astrocytes. J. Biol. Chem. 266:728

Nowell, 1986. Mechanisms of tumor progression. Cancer Res. 46:2203-2207.

Pearson and Choi, 1993. Expression of the human b-amyloid precursor protein gene from a yeast artificial chromosome in transgenic mice. Proc. Natl. Scad. Sci. USA 90:10578-82.

Qian et al, 1993. Cloning of the cDNA encoding and RNA binding protein by screening expression libraries using a Northwestern strategy. Biochemistry 212:547-554.

Radhakrishnan et al., 1990. The automated synthesis of sulfur-containing oligodeoxyribonucleotides using 3*H*-1,2-Benzodithiol-3-One 1,1 Dioxide as a sulfar-transfer reagent. J. Org. Chem. 55:4693-4699. (same as Iyer cite).

Rastinejad et al. 1993. Tumor suppression by RNA from 3' untranslated region of a-tropomyosin. Cell 75:1107-1117.

Reichard, 1993. From RNA to DNA, why so many ribonucleotide reductases? Science 60:1773-1777.

Ross, 1995. mRNA stability in mammalian cells. Microbiol. Rev. 59:423-450.

Rosolen et al., 1990. Antisense Inhibition of Single Copy N-*myc* Expression Results in Decreased Cell Growth Without Reduction of c-*myc* Protein in a Neuropithelioma Cell Line. Cancer Res. 50:6316.

Rothstein, "Targeting, disruption, replacement, and allele rescue: integrative DNA transformation in yeast" in *Methods in Enzymology*, vol. 194, "Guide to Yeast Genetics and Molecular Biology", eds. C. Guthrie and G. Fink, Academic Press, Inc., Chap. 19, pp. 281-301 (1991).

Rowley, 1990. Cytogenetics: Rosetta Stone for understanding cancer. Cancer Res. 50:3816-3825.

Sachs, 1993. Messenger RNA degradation in eukaryotes. Cell 74:413-421.

Saeki et al., 1995. Immunohistochemical detection of ribonucleotide reductase in human breast tumors. Int. J. Oncol. 6:523-529.

Scanlon et al., 1995. Oligonucleotides-mediated modulation of mammalian gene expression. FASEB J. 9:1288.

Schedl et al., "A yeast artificial chromosome covering the tyrosinase gene confers copy number-dependent expression in transgenic mice", *Nature*, vol. 362, pp. 258-261 (1993).

Schwarz, 1988. Loss of growth factor dependence and conversion of transforming growth factor-$b_1$ inhibition to stimulation in metastatic H-*ras* transformed murine fibroblasts. Cancer Res. 48:6999-7003.

Shaw et al., 1991. Modified deoxyoligonucleotides stable to exonuclease degradation in serum. Nucleic Acids Res. 19:747-750.

Spearman et al., 1994. Antisense oligodeoxyribonucleotide inhibition of TGF-$b_1$ gene expression and alterations in the growth and malignant properties of mouse fibrosarcoma cells. Gene 149:25-29.

Spitzer and Eckstein 1988. Inhibition of deoxynucleases by phosphorothioate groups in oligodeoxyribonucleotides. Nucleic Acids Res. 18:11691-11704.

Stokoe et al., 1994. Activation of Raf as a result of recruitment to the plasma membrane. Science 264:1463-1467.

Strauss et al., "Germ line transmission of a yeast artificial chromosome spanning the murine $a_1$ (I) collagen locus", *Science*, vol. 259, pp. 1904-1907 (1993).

Stubbe, 1989. Protein radical involvement in biological catalysis? Annu. Rev. Biochem. 58:257-285.

Taylor et al., 1992. Evidence for synergistic interations between *ras, myc* and a mutant form of p53 in cellular transformation and tumor dissemination. Oncogene 7:1383-1390.

Thelander et al., 1985. Subunit M2 of mammalian ribonucleotide reductase. Characterization of a homogeneous protein isolated from M2-overproducing mouse cells. J. Biol. Chem. 260:2737-2741.

Thelander et al., 1980. Ribonucleotide reductase from calf thymus. Separation of the enzyme into two nonidentical subunits, proteins M1 and M2. J. Biol. Chem. 255:7426-7432.

Thompson et al, 1989. Cell 56:313-321.

Tlsty, 1990. Normal diploid human and rodent cells lack a detectable frequency of gene amplification. Proc. Natl. Acad. Sci. USA 87:3132-3136.

Tonin et al., 1987. Chromosomal assignment of amplified genes in hydroxyurea resistant hamster cells. Cytogenet. Cell Genet. 45:102-108.

Uhlenbeck, 1987. Nature 328:596-600.

Van Der Putten et al, 1985. PNAS USA 82:6145-6152.

Wagner et al., 1996. Potent and selective inhibition of gene expression by an antisense heptanucleotide. Nature Biotechnology 14:840-844.

Wagner, 1994. Gene inhibition using antisense oligodeoxynucleotides. Nature 372:333.

Weber, 1983. Biochemical strategy of cancer cells and the design of chemotherapy. Cancer Res. 43:3466-3492.

Whitesell et al., 1991. Episome-generated N-*myc* antisense RNA restricts the differentiation potential of primitive neuroectodermal cell lines. Mol. Cell. Biol. 11:1360.

Wolman, 1983. Karyotypic progression in human tumors. Cancer Metastasis Rev. 2:257-293.

Woolf et al., 1990. The stability, toxicity and effectiveness of unmodified and phosphorothioate antisense oligodeoxynucleotides in *Xenopus* oocytes and embryos. Nucleic Acids Res. 18:1763-1769.

Wright et al., 1987. Altered Expression of Ribonucleotide Reductase and Role of *M2* Gene Amplification in Hydroxyurea-Resistant Hamster, Mouse, Rat, and Human Cell Lines. Somat. Cell Mol. Genet. 13:155-165.

Wright, 1989A. Altered mammalian ribonucleotide reductase from mutant cell lines. Encycl. Pharmacol. Therapeut. 128:89-111.

Wright et al., 1989B. Hydroxyurea and related compounds. *In*: R.S. Gupta (ed.), Drug Resistance in Mammalian Cells, Boca Raton, FL; CRC Press, Inc; 15-27.

Wright et al., 1990A. Regulation and drug resistance mechanisms of mammalian ribonucleotide reductase and the significance to DNA synthesis. Biochem. Cell Biol. 68:1364-1371.

Wright et al., 1990B. DNA amplification is rare in normal human cells. Proc. Natl. Acad. Sci. USA. 87:1791-1795.

Wright et al., 1993. Transforming growth factor b and fibroblast growth factor as promoters of tumor progression to malignancy. Crit. Rev. Oncogen. 4:473-492.

Wright & Anazodo, 1995. Antisense Molecules and Their Potential For The Treatment Of Cancer and AIDS. Cancer J. 8:185-189.

Yakubov et al, 1989. Mechanism of oligonucleotide uptake by cells: Involvement of specific receptors? PNAS USA 86:6454.

\* cited by examiner

SEQUENCE LISTING

<160> NUMBER OF SEQ ID NOS: 50

<210> SEQ ID NO 1
<211> LENGTH: 523
<212> TYPE: DNA
<213> ORGANISM: Homo sapiens

<400> SEQUENCE: 1

```
ggaaagactt ggaagagacc agcatgtctt cagtagccaa actacttctt gagcatagat      60
aggtatagtg ggtttgcttg aggtggtaag gctttgctgg accctgttgc aggcaaaagg     120
agtaattgat ttaaagtact gttaatgatg ttaatgattt ttttttaaac tcatatattg     180
ggattttcac caaaataatg cttttgaaaa aaagaaaaaa aaaacggata tattgagaat     240
caaagtagaa gttttaggaa tgcaaaataa gtcatcttgc atacagggag tggttaagta     300
aggtttcatc acccatttag catgcttttc tgaagacttc agtttttgtta aggagattta    360 gttttactgc tttgactggt gggtctctag aagcaaaact gagtgataac tcatgagaag     420
tactgatagg acctttatct ggatatggtc ctataggtta ttctgaaata aagataaaca     480
tttctaagtg aaaaaaaaaa aaaaaaaaaa aaaaaaaaaa aaa                       523
```

<210> SEQ ID NO 2
<211> LENGTH: 1136
<212> TYPE: DNA
<213> ORGANISM: Homo sapiens

<400> SEQUENCE: 2

-continued

| | |
|---|---|
| atgaactgaa gatgtgccct tacttggctg attttttttt tccatctcat aagaaaaatc | 60 |
| agctgaagtg ttaccaacta gccacaccat gaattgtccg taatgttcat taacagcatc | 120 |
| tttaaaactg tgtagctacc tcacaaccag tcctgtctgt ttatagtgct ggtagtatca | 180 |
| ccttttgcca gaaggcctgg ctggctgtga cttaccatag cagtgacaat ggcagtcttg | 240 |
| gctttaaagt gaggggtgac cctttagtga gcttagcaca gcggattaa acagtccttt | 300 |
| aaccagcaca gccagttaaa agatgcagcc tcactgcttc aacgcagatt ttaatgttta | 360 |
| cttaaatata aacctggcac tttacaaaca aataaacatt gttttgtact cacggcggcg | 420 |
| ataatagctt gatttatttg gtttctacac caaatacatt ctcctgacca ctaatgggag | 480 |
| ccaattcaca attcactaag tgactaaagt aagttaaact tgtgtagact aagcatgtaa | 540 |
| ttttttaagtt ttatttttaat gaattaaaat atttgttaac caactttaaa gtcagtcctg | 600 |
| tgtataccta gatattagtc agttggtgcc agatagaaga caggttgtgt ttttatcctg | 660 |
| tggcttgtgt agtgtcctgg gattctctgc cccctctgag tagagtgttg tgggataaag | 720 |
| gaatctctca gggcaaggag cttcttaagt taaatcacta gaaatttagg ggtgatctgg | 780 |
| gccttcatat gtgtgagaag ccgtttcatt ttatttctca ctgtatttc ctcaacgtct | 840 |
| ggttgatgag aaaaaattct tgaagagttt tcatatgtgg gagctaaggt agtattgtaa | 900 |
| aatttcaagt catccttaaa caaaatgatc cacctaagat cttgccctg ttaagtggtg | 960 |
| aaatcaacta gaggtggttc ctacaagttg ttcattctag ttttgtttgg tgtaagtagg | 1020 |
| ttgtgtgagt taattcattt atatttacta tgtctgttaa atcagaaatt ttttattatc | 1080 |
| tatgttcttc tagattttac ctgtagttca taaaaaaaaa aaaaaaaaaa aaaaaa | 1136 |

<210> SEQ ID NO 3
<211> LENGTH: 20
<212> TYPE: DNA
<213> ORGANISM: Homo sapiens

<400> SEQUENCE: 3
ggatttaggt gacactatag                                           20

<210> SEQ ID NO 4
<211> LENGTH: 18
<212> TYPE: DNA
<213> ORGANISM: Homo sapiens

<400> SEQUENCE: 4
tgagaaaagc ggggcctg                                             18

<210> SEQ ID NO 5
<211> LENGTH: 21
<212> TYPE: DNA
<213> ORGANISM: Homo sapiens

<400> SEQUENCE: 5
taagtaactg atcgtgtgct c                                         21

<210> SEQ ID NO 6
<211> LENGTH: 20
<212> TYPE: DNA
<213> ORGANISM: Homo sapiens

<400> SEQUENCE: 6
gagttttcat atgtgggagc                                           20

```
<210> SEQ ID NO 7
<211> LENGTH: 20
<212> TYPE: DNA
<213> ORGANISM: Homo sapiens

<400> SEQUENCE: 7
gagttttctc atatgtggga                                              20

<210> SEQ ID NO 8
<211> LENGTH: 20
<212> TYPE: DNA
<213> ORGANISM: Homo sapiens

<400> SEQUENCE: 8
aatgaactga agatgtgccc                                              20

<210> SEQ ID NO 9
<211> LENGTH: 20
<212> TYPE: DNA
<213> ORGANISM: Homo sapiens

<400> SEQUENCE: 9
aggaatctct cagggcaagg                                              20

<210> SEQ ID NO 10
<211> LENGTH: 20
<212> TYPE: DNA
<213> ORGANISM: Homo sapiens

<400> SEQUENCE: 10
gcttgattta tttggtttct                                              20

<210> SEQ ID NO 11
<211> LENGTH: 20
<212> TYPE: DNA
<213> ORGANISM: Homo sapiens

<400> SEQUENCE: 11
gccagataga agacaggttg                                              20

<210> SEQ ID NO 12
<211> LENGTH: 20
<212> TYPE: DNA
<213> ORGANISM: Homo sapiens

<400> SEQUENCE: 12
atcctgtggc ttgtgtagtg                                              20

<210> SEQ ID NO 13
<211> LENGTH: 20
<212> TYPE: DNA
<213> ORGANISM: Homo sapiens

<400> SEQUENCE: 13
tttttttttt ccatctcata                                              20

<210> SEQ ID NO 14
<211> LENGTH: 20
<212> TYPE: DNA
<213> ORGANISM: Homo sapiens

<400> SEQUENCE: 14
ctggctggct gtgacttacc                                              20
```

```
<210> SEQ ID NO 15
<211> LENGTH: 20
<212> TYPE: DNA
<213> ORGANISM: Homo sapiens

<400> SEQUENCE: 15
actcacggcg gcgataatag                                               20

<210> SEQ ID NO 16
<211> LENGTH: 20
<212> TYPE: DNA
<213> ORGANISM: Homo sapiens

<400> SEQUENCE: 16
atacattctc ctgaccacta                                               20

<210> SEQ ID NO 17
<211> LENGTH: 20
<212> TYPE: DNA
<213> ORGANISM: Homo sapiens

<400> SEQUENCE: 17
ggttgtgttt ttatcctgtg                                               20

<210> SEQ ID NO 18
<211> LENGTH: 20
<212> TYPE: DNA
<213> ORGANISM: Homo sapiens

<400> SEQUENCE: 18
gtttttatcc tgtggcttgt                                               20

<210> SEQ ID NO 19
<211> LENGTH: 20
<212> TYPE: DNA
<213> ORGANISM: Homo sapiens

<400> SEQUENCE: 19
gtggcttgtg tagtgtcctg                                               20

<210> SEQ ID NO 20
<211> LENGTH: 20
<212> TYPE: DNA
<213> ORGANISM: Homo sapiens

<400> SEQUENCE: 20
ctgagtagag tgttgtggga                                               20

<210> SEQ ID NO 21
<211> LENGTH: 20
<212> TYPE: DNA
<213> ORGANISM: Homo sapiens

<400> SEQUENCE: 21
gtgttgtggg ataaaggaat                                               20

<210> SEQ ID NO 22
<211> LENGTH: 20
<212> TYPE: DNA
<213> ORGANISM: Homo sapiens

<400> SEQUENCE: 22
tctcactgta ttttcctcaa                                               20
```

<210> SEQ ID NO 23
<211> LENGTH: 20
<212> TYPE: DNA
<213> ORGANISM: Homo sapiens

<400> SEQUENCE: 23
ggtgtaagta ggttgtgtga                                         20

<210> SEQ ID NO 24
<211> LENGTH: 20
<212> TYPE: DNA
<213> ORGANISM: Homo sapiens

<400> SEQUENCE: 24
ataaaggaat ctctcagggc                                         20

<210> SEQ ID NO 25
<211> LENGTH: 20
<212> TYPE: DNA
<213> ORGANISM: Homo sapiens

<400> SEQUENCE: 25
tactcacggc ggcgataata                                         20

<210> SEQ ID NO 26
<211> LENGTH: 20
<212> TYPE: DNA
<213> ORGANISM: Homo sapiens

<400> SEQUENCE: 26
atagcagtga caatggcagt                                         20

<210> SEQ ID NO 27
<211> LENGTH: 20
<212> TYPE: DNA
<213> ORGANISM: Homo sapiens

<400> SEQUENCE: 27
cttaccatag cagtgacaat                                         20

<210> SEQ ID NO 28
<211> LENGTH: 20
<212> TYPE: DNA
<213> ORGANISM: Homo sapiens

<400> SEQUENCE: 28
gctacctcac aaccagtcct                                         20

<210> SEQ ID NO 29
<211> LENGTH: 20
<212> TYPE: DNA
<213> ORGANISM: Homo sapiens

<400> SEQUENCE: 29
acttggctga tttttttttt                                         20

<210> SEQ ID NO 30
<211> LENGTH: 21
<212> TYPE: DNA
<213> ORGANISM: Homo sapiens

<400> SEQUENCE: 30

-continued cctggctggc tgtgacttac c                                              21

<210> SEQ ID NO 31
<211> LENGTH: 21
<212> TYPE: DNA
<213> ORGANISM: Homo sapiens

<400> SEQUENCE: 31
atacattctc ctgaccacta a                                              21

<210> SEQ ID NO 32
<211> LENGTH: 22
<212> TYPE: DNA
<213> ORGANISM: Homo sapiens

<400> SEQUENCE: 32
gtagtatcac cttttgccag aa                                             22

<210> SEQ ID NO 33
<211> LENGTH: 23
<212> TYPE: DNA
<213> ORGANISM: Homo sapiens

<400> SEQUENCE: 33
ggtgccagat agaagacagg ttg                                            23

<210> SEQ ID NO 34
<211> LENGTH: 24
<212> TYPE: DNA
<213> ORGANISM: Homo sapiens

<400> SEQUENCE: 34
ctaaatgaac tgaagatgtg ccct                                           24

<210> SEQ ID NO 35
<211> LENGTH: 24
<212> TYPE: DNA
<213> ORGANISM: Homo sapiens

<400> SEQUENCE: 35
gcttgattta tttggtttct acac                                           24

<210> SEQ ID NO 36
<211> LENGTH: 25
<212> TYPE: DNA
<213> ORGANISM: Homo sapiens

<400> SEQUENCE: 36
ataaaggaat ctctcagggc aagga                                          25

<210> SEQ ID NO 37
<211> LENGTH: 25
<212> TYPE: DNA
<213> ORGANISM: Homo sapiens

<400> SEQUENCE: 37 atttttttatt atctatgttc ttcta                                         25

<210> SEQ ID NO 38
<211> LENGTH: 27
<212> TYPE: DNA
<213> ORGANISM: Homo sapiens

<400> SEQUENCE: 38

```
cccttacttg gctgatttt tttttcc                                    27
```

<210> SEQ ID NO 39
<211> LENGTH: 29
<212> TYPE: DNA
<213> ORGANISM: Homo sapiens

<400> SEQUENCE: 39

```
ctgagtagag tgttgtggga taaaggaat                                 29
```

<210> SEQ ID NO 40
<211> LENGTH: 38
<212> TYPE: DNA
<213> ORGANISM: Homo sapiens

<400> SEQUENCE: 40

```
aagccgtttc attttatttc tcactgtatt ttcctcaa                       38
```

<210> SEQ ID NO 41
<211> LENGTH: 34
<212> TYPE: DNA
<213> ORGANISM: Homo sapiens

<400> SEQUENCE: 41

```
tagttttgtt tggtgtaagt aggttgtgtg agtt                           34
```

<210> SEQ ID NO 42
<211> LENGTH: 37
<212> TYPE: DNA
<213> ORGANISM: Homo sapiens

<400> SEQUENCE: 42

```
acctgtagtt cataaaaaaa aaaaaaaaa aaaaaaa                         37
```

<210> SEQ ID NO 43
<211> LENGTH: 39
<212> TYPE: DNA
<213> ORGANISM: Homo sapiens

<400> SEQUENCE: 43

```
ggttgtgttt ttatcctgtg gcttgtgtag tgtcctggg                      39
```

<210> SEQ ID NO 44
<211> LENGTH: 20
<212> TYPE: DNA
<213> ORGANISM: Homo sapiens

<400> SEQUENCE: 44

```
agtgggtttg cttgaggtgg                                           20
```

<210> SEQ ID NO 45
<211> LENGTH: 20
<212> TYPE: DNA
<213> ORGANISM: Homo sapiens

<400> SEQUENCE: 45

```
ggctttgctg gaccctgttg                                           20
```

<210> SEQ ID NO 46
<211> LENGTH: 20
<212> TYPE: DNA
<213> ORGANISM: Homo sapiens

```
<400> SEQUENCE: 46
aaaaaaagaa aaaaaaaacg                                          20

<210> SEQ ID NO 47
<211> LENGTH: 20
<212> TYPE: DNA
<213> ORGANISM: Homo sapiens

<400> SEQUENCE: 47
agtagaagtt ttaggaatgc                                          20

<210> SEQ ID NO 48
<211> LENGTH: 20
<212> TYPE: DNA
<213> ORGANISM: Homo sapiens

<400> SEQUENCE: 48
gtttcatcac ccatttagca                                          20

<210> SEQ ID NO 49
<211> LENGTH: 20
<212> TYPE: DNA
<213> ORGANISM: Homo sapiens

<400> SEQUENCE: 49
tttactgctt tgactggtgg                                          20

<210> SEQ ID NO 50
<211> LENGTH: 21
<212> TYPE: DNA
<213> ORGANISM: Homo sapiens

<400> SEQUENCE: 50
ttaagacttt ttacgcgatt c                                        21
```

OLIGONUCLEOTIDES FROM THE UNTRANSLATED REGIONS OF HOUSEKEEPING GENES AND METHODS OF USING SAME TO MODULATE CELL GROWTH

CROSS-REFERENCE TO RELATED APPLICATIONS

This application is the National Stage of International Application No. PCT/CA97/00454, filed Jun. 30, 1997, which claims the benefit of U.S. provisional Application No. 60/021,152, filed Jul. 1, 1996.

FIELD OF THE INVENTION

The invention relates to oligonucleotides from the untranslated regions of housekeeping genes, and methods and compositions for modulating cell growth and differentiation using same. Specifically it relates to the use of the untranslated regions (UTR) from housekeeping genes specifically the R1 and R2 components of ribonucleotide reductase UTR, for inhibiting tumor cell growth and metastasis.

BACKGROUND OF THE INVENTION

The first unique step leading to DNA synthesis is the conversion of ribonucleotides to their corresponding deoxyribonucleotides, a reaction that is catalyzed in a cell cycle specific manner by the housekeeping gene ribonucleotide reductase [Lewis et al., 1978; Reichard, 1993; Wright, 1989a; Wright et al., 1990a; Stubbe, 1989]. The mammalian enzyme is composed of two dissimilar dimeric protein components often called R1 and R2, which are encoded by two different genes located on different chromosomes [Björklund et al., 1993; Tonin et al., 1987]. Mammalian protein R1 is a homodimeric structure, with a molecular weight of about 170 kDa, and has substrate sites and allosteric effector sites that control enzyme activity and substrate specificity [Wright, 1989; Thelander et al., 1980; Caras et al., 1985; Wright et al., 1990a]. Protein R2 is a homodimer, with a molecular weight of 88 KDa, and forms two equivalent dinuclear iron centers that stabilizes a tyrosyl free radical required for catalysis [Wright et al., 1990a; Thelander et al., 1985; McClarty et al., 1990]. R1 and R2 proteins interact at their C-terminal ends to form an active holoenzyme [Reichard, 1993; Wright et al., 1990a; Davis et al., 1994].

R1 and R2 are differentially regulated during the cell cycle. There is an S-phase correlated increase in the R2 protein resulting from its de novo synthesis [Lewis et al., 1978; Mann et al., 1988]. The activity of ribonucleotide reductase, and therefore DNA synthesis and cell proliferation, is controlled in proliferating cells during the cell cycle by the synthesis and degradation of the R2 component [Eriksson et al., 1984]. The rate-limiting R2 component is a phosphoprotein capable of being phosphorylated by the CDC2 and CDK2 protein kinase mediators of cell cycle progression [Chan et al., 1993], and contains non-heme iron that stabilizes an unique tyrosyl free radical required for enzyme activity [Reichard, 1993; McClarty et al., 1990].

The levels of the R1 protein do not appear to change substantially during the cell cycle of proliferating cells and can be detected throughout the cell cycle. Synthesis of R1 mRNA, like R2 mRNA appears to occur mainly during S phase [Eriksson et al., 1984; Choy et al., 1988; Mann et al., 1988]. The broader distribution of the R1 protein during the cell cycle is attributed to its longer half life as compared to the R2 protein [Choy et al., 1988; Mann et al., 1988.

Regulation of ribonucleotide reductase, and particularly the R2 component, is markedly altered in malignant cells exposed to tumor promoters or to the growth factor TGF-β [Amara, et al., 1994; Chen et al., 1993; Amara et al., 1995b; Hurta and Wright, 1995; Hurta et al., 1991]. Higher levels of enzyme activity have been observed in cultured malignant cells when compared to nonmalignant cells [Weber, 1983; Takeda and Weber, 1981; Wright et al., 1989a], and increased levels of R2 protein and R2 mRNA have been found in pre-malignant and malignant tissues as compared to normal control tissue samples [Saeki et al., 1995; Jensen et al., 1994]. Regulation of ribonucleotide reductase, and in particular the R2 component, is significantly elevated in transformed cells exposed to tumor promoters, or to transforming growth factor β in growth factor mediated mechanisms of tumor progression [Amara et al., 1996; Chen et al., 1993; Amara et al, 1995b]. These studies are in tumor cells obtained from rodent and human tissues [Weber, 1983; Wright et al., 1989a; Saeki, et al., 1995; Jenson et al, 1994], and in cultured cells selected for resistance to anti-tumor agents such as hydroxyurea [Lewis et al., 1978; Wright et al., 1989b].

Chemotherapeutic compounds like hydroxyurea inhibit ribonucleotide reductase activity by destabilizing the iron centre of the R2 protein causing the destruction of the tyrosyl free radical [McClarty et al., 1990], and preventing cells from progressing through S-phase of the cell cycle [Ashihara and Baserga, 1979]. In addition to cell cycle control, ribonucleotide reductase can be regulated by an S-phase independent mechanism that is important for DNA repair. Ribonucleotide reductase activity can be induced outside the S phase by DNA cross-linking agents such as chlorambucil, and by UV irradiation indicating a role for the enzyme in the DNA repair process [Hurta and Wright, 1992; Filatov, et al., 1996].

Recent studies have shown that ribonucleotide reductase activity is quickly elevated in the presence of tumor promoters like 12-0-tetradecanoylphorbol-13-acetate [Amara et al., 1994; Chen et al., 1993]. This process is mediated at least in part, through increases in the half-lives of R1 and R2 mRNAs, which parallels the decreased interactions of two proteins, R1BP and R2BP, with cis-element sequences in the 3' untranslated regions (3' UTRs) of the R1 and R2 messages [Amara et al., 1994; Chen et al., 1993; Chen et al., 1994a; Chen et al., 1994b]. Alterations in this cis-trans reaction can play a role in determining sensitivity to chemotherapeutic agents that target ribonucleotide reductase [Amara et al., 1995a].

Exposure of transformed fibroblasts to TGF-$\beta_1$ can increase the half-life of the R2 message, a process that is mediated through a cis-trans interaction within the R2 mRNA 3' UTR [Amara et al., 1995b; Hurta and Wright, 1995]. Other studies have demonstrated that the non-coding regions of mRNAs can control important biological properties of cells, such as the expression of bFGF in Xenopus oocytes [Kimelman and Kirschner, 1989], the timing of developmental events of *Caenorhabditis elegans* [Lee et al., 1993], the expression of α1 (I) collagen in chick embryo chondrocytes [Farrell and Lukens, 1995], and the suppression of tumorigenicity of rhabdomyosarcomas by RNA from the 3' UTR of the non-housekeeping gene α-tropomyosin [Rastinejad et al., 1993].

PCT patent application WO 94/21661 discusses the use of UTRs of cell structural proteins to regulate cell division or cell differentiation and provides a discussion of how exogenous UTR may affect cell regulation. The application in particular relates to UTRs of α-tropomyosin.

The regulation of mRNA turnover is an essential step in controlling message abundance and therefore gene expression in mammalian cells. Message degradation or stability plays a critical role in cell proliferation or cellular differentiation, and is crucial in mechanisms that maintain normal biological functions of individual cells and tissues. Aberrant mRNA turnover usually leads to altered levels of proteins, which can dramatically modify cellular properties. For example, oncogene or growth factor overexpression is often associated with abnormal cell proliferation and malignant transformation. Since message turnover is an important component of gene regulation, it is not surprising to find that message stability characteristics of key growth regulatory genes are tightly controlled. Several excellent reviews are available which describe in detail mechanisms of gene expression that are regulated at the mRNA level [Ross, 1995; Hake and Richer, 1997].

Messenger RNA is composed of distinct domains that either encode proteins or carry specific regulatory regions that control gene expression posttranscriptionally. Structurally there are three distinct regions of an mRNA molecule, the 5' end including the cap (5'-GpppG--), the coding region, and the 3' end including the polyadenylated tail. The structural elements of mRNA are known to play integral roles in mechanisms regulating translation and mRNA stability, which in turn directly affect translation efficiency and the turnover rate of the message, and therefore the amount of a specific protein that is synthesized.

The 5' end of an mRNA molecule contains a sequence that is not translated into protein and therefore is known as the 5' untranslated region (UTR), and contains the mRNA cap which confers nuclease resistance properties. There is a great deal of evidence showing that the 5' end of a message is critically involved in regulating translation initiation [Ross, 1995; Hake and Richer, 1997]. Alterations in translation regulation not only directly affects the amount of a protein that is eventually synthesized, but it can also significantly modify the stability characteristics of the message and therefore modify protein levels by this mechanism as well. For example, some viruses are capable of modifying the binding of regulatory proteins to the 5' UTR including the cap region, and through this process control host versus virus gene expression. The 5' UTR of a message can be relatively short or can be several hundred nucleotides in length.

There is also a region of varying length following the coding sequence that is not translated into protein, and this 3' UTR which may be many hundreds of nucleotides in length, appears to play a dominant role in determining message stability characteristics. There are now many examples of unique cis-elements in this part of the message that bind to trans-acting proteins to control mRNA turnover rates [Ross, 1995; Hake and Richer, 1997].

In addition, most mRNAs have a polyadenylated (poly (A)) tail at the 3 end, which can serve several functions important to translation efficiency and message turnover characteristics. For example the poly (A) tail protects the message from degradation in some systems, and it has been demonstrated that deadenylation may be the first step in message degradation. The mere presence of a poly (A) tail is not necessarily sufficient for protection, instead the poly (A) tail should be a minimum length, for example 20 to 30 nucleotides long, to provide protection from nuclease action. When the number of residues is changed experimentally, the rate of degradation can be increased or decreased by the absence or presence of a specific number of residues. Several proteins are involved in this regulation including a poly (A) binding protein, and it has been suggested that the poly (A) tail blocks the assembly of an exonuclease involved in RNA degradation [Sachs, 1993; Ford et al., 1997].

Besides the interactions between cis-elements with precise nucleotide sequences and trans-acting proteins, secondary structural conformations such as stem-loops and hairpin structures also serve regulatory functions in the untranslated regions (UTRs) of mRNAs. For example, it has been shown in some cases, that it is possible to transfer sequences containing interesting structural features from the UTR from one mRNA to another and alter the stability characteristics of the recipient mRNA. Certainly, stem-loop structures play important roles in message regulation of histone mRNA [Marzluff and Pandey, 1988], or ferritin and transferrin receptor mRNA regulation [Klausner and Hartford, 1989]. Histone mRNAs are cell cycle regulated and lack a poly (A) tail, but structural information in the 3' UTR including a 6 base pair stem and 4 base loop motif found in all histone mRNAs, play crucial roles in controlling the rates of translation and degradation. In general, secondary structural features are important because they influence the binding of regulatory proteins that directly or indirectly affect interactions between the mRNA and nucleases and/or because they may act directly as favored recognition sites for particular nuclease activities or as inhibitors of nuclease action.

The genetic changes underlying cancer conversion and progression are accompanied by a decrease in genomic stability of cells [Cifone and Fidler, 1981; Wolman, 1983; Rowley, 1990; Huang et al., 1995a], which leads to heterogeneity of tumor cell populations, alterations in response to chemotherapy, and increased malignant potential. The multitude of changes that are observed during malignant transformation and are most pronounced at advanced stages of the disease, are at least in part due to changes in genome/ message stability, as manifested for example by an increased potential for DNA amplification [Rowley, 1990; Wright et al., 1990b; Tlsty, 1990]. Normal diploid cells rarely amplify their DNA, but amplification of oncogenes and genes determining drug resistance is often observed in tumor cell populations, and this is one of the most impressive characteristics that distinguishes normal cells from tumor cells [Wright et al., 1990b; Tlsty, 1990]. The expression of several genes that are known to play fundamental roles in malignant progression are strictly regulated at the posttranscriptional level through mechanisms that control message stability characteristics. Clearly, mechanisms that lead to genomic/ message destabilization are important in cancer transformation and progression, and methods are needed for reversing or controlling genomic destabilization which can be utilized in treating cancer.

SUMMARY OF THE INVENTION

The present inventors have shown by direct evidence that untranslated regions of a housekeeping gene, in particular ribonucleotide reductase R1 and R2, significantly reduces tumor growth rates in animals. They have also directly shown that untranslated regions of housekeeping genes, in particular ribonucleotide reductase R2 reduces the ability of tumor cells to metastasize.

Accordingly broadly stated the present invention relates to an isolated oligonucleotide comprising at least seven consecutive nucleotides or nucleotide analogues from an untranslated region from a housekeeping gene. Preferably the housekeeping gene is ribonucleotide reductase R1 or R2.

In one embodiment the oligonucleotide comprises at least seven nucleotides or nucleotide analogues from the 3' untranslated region of ribonucleotide reductase R1 as shown in SEQ ID NO 1, preferably an oligonucleotide having the nucleic acid sequence shown in SEQ. ID NO 44, SEQ. ID NO 45, SEQ. ID NO 46, SEQ. ID NO 47, SEQ. ID NO 48, or SEQ. ID NO 49, or an analogue thereof. In another embodiment, the oligonucleotide comprises at least seven nucleotides or nucleotide analogues from the 3' untranslated region of ribonucleotide reductase R2 as shown in SEQ ID NO 2, preferably an oligonucleotide having the nucleic acid sequence shown in SEQ. ID NO 6 through SEQ. ID. NO. 43, or an analogue thereof.

The invention also includes an antisense oligonucleotide having a sequence complementary to the sequence of a oligonucleotide of the invention, or a ribozyme sequence which has a homologous or complementary sequence to a oligonucleotide of the invention and the necessary catalytic center for cleaving the oligonucleotide.

DNA sequences comprising a transcriptional control region and a sequence encoding an oligonucleotide, antisense oligonucleotide, or ribozyme sequence of the invention, and vectors comprising the DNA sequences are also contemplated.

The invention also provides a pharmaceutical composition for modulating cell growth, in particular tumor cell growth comprising at least one oligonucleotide, antisense oligonucleotide, and ribozyme sequence, of the invention in admixture with a physiologically acceptable carrier or diluent.

The invention still further provides a pharmaceutical composition for reducing the ability of a cell to metastasize comprising at least one oligonucleotide, antisense oligonucleotide, and ribozyme sequence from the untranslated region of ribonucleotide reductase R2, in admixture with a physiologically acceptable carrier or diluent.

The invention also contemplates the use of an oligonucleotide according to the invention to prepare a medicament for modulating cell growth and in particular tumor cell growth, and for reducing the ability of a tumor cell to metastasize.

A method is also provided for identifying a substance that modulates tumor cell growth or metastasis comprising: (a) reacting a test substance with an oligonucleotide comprising at least 7 consecutive nucleotides or nucleotide analogues of an untranslated region of mRNA of a housekeeping gene, under conditions which permit the formation of complexes between the test substance and oligonucleotide, and (b) assaying for complexes, for free substance, and/or for non-complexed oligonucleotide to determine if the substance binds to the oligonucleotide and thereby modulates tumor cell growth or metastasis.

Further a method is provided for evaluating a compound for the ability to inhibit or enhance the interaction of an oligonucleotide of the invention with a substance which binds to the oligonucleotide and thereby modulate tumor cell growth or metastasis comprising: (a) providing a known concentration of the oligonucleotide and a substance which is capable of binding to the oligonucleotide, and a candidate compound under conditions which permit the formation of complexes between the substance and oligonucleotide, and (b) assaying for complexes, for free substance, and/or for non-complexed oligonucleotide to determine if the compound inhibits or enhances the interaction of the substance and oligonucleotide, and thereby modulates tumor cell growth or metastasis.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Oligonucleotides, Antisense, and Ribozymes

Figure 1:
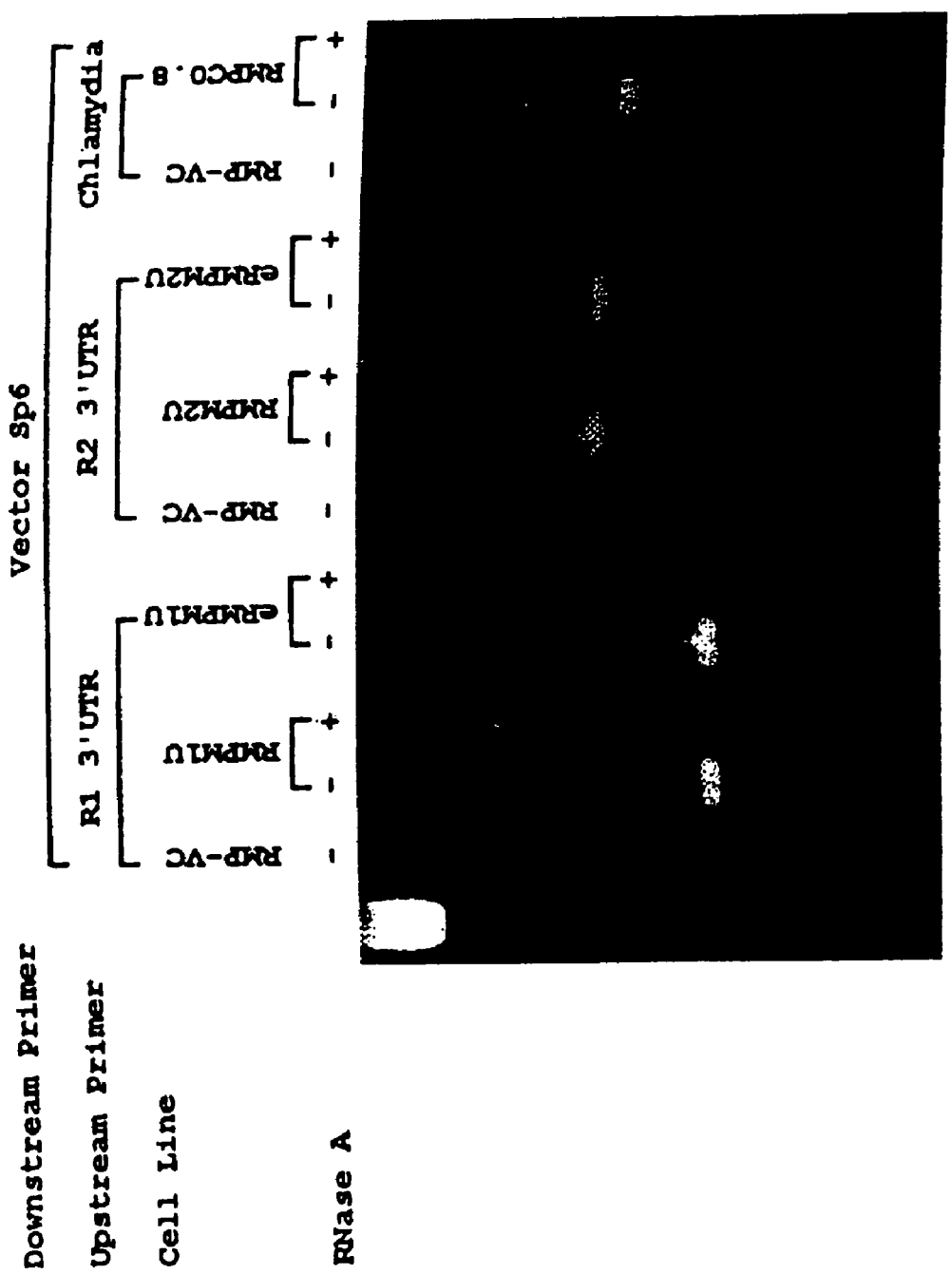
FIG. 1 is a photograph of a gel showing the expression of recombinant 3' UTRs in vector-transfected RMP-6 cells (Example 1)

The present invention relates to oligonucleotides which modulate cell growth and differentiation which comprises an untranslated region (UTR) from a housekeeping gene. A reduction or inhibition of tumor cell growth is a preferred form of modulation contemplated by the invention. The reduction or inhibition of tumor cell growth may be evidenced by the tumor cells exhibiting a differentiated normal growth pattern (i.e. normal cell division and growth) and/or killing of the tumor cells. Particular types of oligonucleotides of the invention have also been found to modulate metastasis i.e. the spread of tumor cells from one part of the body to another as in the appearance of tumor cells in parts of the body remote from the site of the primary tumor, resulting from dissemination of tumor cells by the lymphatics or blood vessels or by direct extension of tumor cells through serous cavities or subarachnoid or other spaces.

The term "oligonucleotides" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

Oligonucleotides of the present invention may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an oligonucleotide. Oligonucleotides may also have sugar mimetics.

The oligonucleotides may be selected such that they exhibit the least likelihood of dimer formation, self-complementary interactions, and binding potential to the UTR sequence. These properties may be determined using the computer modeling program OLIGO Primer Analysis software Version 3.4 (National Biosciences). The program allows the determination of a qualitative estimation of these three parameters and indicates "no potential"; "some potential"; or "essentially complete potential". Oligonucleotides are preferably selected that have estimates of "some potential" or "no potential", most preferably "no potential", in all three parameters. The oligonucleotides are also selected so that their function is not substantially affected by any modifications or substitutions. It is preferred that the native conformation of the oligonucleotide be retained.

The term "housekeeping gene" as used herein refers to genes/functions/activities that are required by most cycling cells and critically linked to general cell metabolism as opposed to "luxury" genes/functions/activities that are used by specialized cells and tissues of a multicellular organism [see in general "Molecular Biology of the Gene", Alberts et al., Garland Publishing Inc., New York, 1983; "Explorations in Developmental Biology" (Eds C. Fulton and A. O. Klein) Vail-Ballou Press, Inc. 1976; "Principles of Genetics" Herskowitz, The Macmillian Company, New York, 1973]. The housekeeping gene may be associated with DNA and RNA synthesis and cell metabolism. In particular, it may encode a protein regulating DNA synthesis and repair and it may be involved in purine and pyrimidine synthesis. The housekeeping gene may be selected from any housekeeping gene including ribonucleotide reductase which is involved in the conversion of ribonucleotides to their corresponding deoxyribonucleotides; ornithine decarboxylase (ODC) which encodes an enzyme involved in the synthesis of polyamines which are necessary for cell proliferation and survival; CAD which encodes a multi-functional protein containing carbamyl phosphate synthetase, aspartate transcarbamylase and dihydroorotase activity; and dihydrofolate reductase which encodes an enzyme involved in the reduction of the vitamin folic acid to its active form tetrahydrofolate which is involved in the synthesis of thymidylic acid, a nucleotide building block of DNA. Examples of housekeeping genes are shown in Table 3. A preferred housekeeping gene of the present invention is ribonucleotide reductase which is involved in the conversion of ribonucleotides to their corresponding deoxyribonucleotides.

The oligonucleotides may be from any untranslated region of a housekeeping gene. The oligonucleotides may comprise the entire 3' or 5' untranslated regions, or parts thereof. The oligonucleotides may be ribonucleotides or deoxyribonucleotides, and they may be single stranded or doubled stranded.

The oligonucleotides are typically at least seven consecutive nucleotides from a UTR of a housekeeping gene, usually at least 15 consecutive nucleotides, and preferably at least 20 consecutive nucleotides, from a UTR of a housekeeping gene. In one embodiment, the oligonucleotide comprises at least seven consecutive nucleotides from an untranslated region from ribonucleotide reductase R1 or R2. The untranslated region is preferably the entire 3' UTR from mRNA of ribonucleotide reductase R1 or R2 (SEQ. ID. NO. 1 or 2, respectively), or at least seven consecutive nucleotides thereof. Examples of oligonucleotides of the invention are found in Tables 4 and 5. The invention also includes the oligonucleotides as shown in Tables 4 and 5 with mutations. The mutations may be substitutions, insertions, and deletions, and there will usually be fewer than 10% changes. Preferably the oligonucleotide has a sequence identified in one of SEQ. ID. NOs: 1, 2, 6–48, or 49, most preferably 6–12, or 45.

In the oligonucleotides of the invention, an antisense sequence may be used instead of or in addition to a native sequence (i.e. either in the 5' to 3' or 3' to 5' direction) to provide an antisense oligonucleotide. The antisense sequence may comprise naturally occurring nucleotides or modified or substituted nucleotides as described herein. The antisense sequence may be used to inhibit or enhance the effect of an oligonucleotide of the invention. In an embodiment of the invention, the antisense oligonucleotide comprises a sequence complementary to the entire UTR.

A ribozyme sequence which cleaves the UTR may also be used to modulate the activity of an oligonucleotides of the invention. (See Cech for a review of ribozymes). The ribozyme has homologous or complementary sequences to an oligonucleotide of the invention and the necessary catalytic centre for cleaving the oligonucleotide. For example, a homologous ribozyme sequence may be selected which destroys an oligonucleotide of the invention. In an embodiment of the invention the ribozyme sequence is complementary to or homologous to the UTR from ribonucleotide reductase R1 or R2 or parts thereof.

The ribozyme type utilized in the present invention may be selected from types known in the art. Several ribozyme structural families have been identified including Group I introns, RNase P, the hepatitis delta virus ribozyme, hammerhead ribozymes, and the hairpin ribozyme originally derived from the negative strand of the tobacco ringspot virus satellite RNA (sTRSV) (Sullivan, 1994, U.S. Pat. No. 5,225,347, columns 4 to 5). The latter two families are derived from viroids and virusoids, in which the ribozyme is believed to separate monomers form oligomers created during rolling circle replication (Symons, 1989 and 1992). Hammerhead and hairpin ribozyme motifs are most commonly adapted for trans-cleavage of mRNAs for gene therapy (Sullivan, 1994). Hairpin ribozymes which are presently in clinical trials are preferably used in the present invention. In general the ribozyme is from 30 to 100 nucleotides in length.

The oligonucleotides of the invention may be prepared by conventional and well-known techniques. For example, the oligonucleotides may be prepared using solid-phase synthesis and in particular using commercially available equipment such as the equipment available form Applied Biosystems. It is also preferred to substantially purify the oligonucleotides so that they are free of any other factors which would interfere with their activity. Oligonucleotides of the invention may also be identified using genetic complementation techniques, or using the probes described herein. It is also well within the skill in the art to prepare modified or substituted oligonucleotides, antisense oligonucleotides, and ribozymes.

Applications

Probes

The oligonucleotides of the invention allow those skilled in the art to construct nucleotide probes for use in the detection (e.g. by hybridization or polymerase chain reaction (PCR) techniques) of homologous untranslated regions in cells, tissues and biological materials. Hence, the probes can be used to screen for other UTRs having cell growth modulating, preferably tumor growth reducing or inhibiting, activity. Suitable probes include nucleic acid molecules based on nucleic acid sequences from regions of the 3' UTR of ribonucleotide reductase R1 or R2 as shown in Tables 4 and 5. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect preferably in human cells nucleic acid molecules from UTRs of housekeeping genes that modulate cell growth, in particular tumor cell growth.

Antibodies

Oligonucleotides of the invention can be used to prepare antibodies. Conventional methods can be used to prepare the antibodies. Antibodies to nucleic acids are described in U.S. Pat. No. 4,732,847. For example, polyclonal antisera or monoclonal antibodies can be made using standard methods. A mammal, (e.g., a mouse, hamster, or rabbit) can be immunized with an immunogenic form of the oligonucleotide which elicits an antibody response in the mammal. Techniques for conferring immunogenicity on an oligonucleotide include conjugation to carriers or other techniques well known in the art. For example, the oligonucleotide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the oligonucleotide and the monoclonal antibodies can be isolated. Therefore, the invention also contemplates hybridoma cells secreting monoclonal antibodies with specificity for the oligonucleotides of the invention.

The term "antibody" as used herein is intended to include fragments thereof which also specifically react with the oligonucleotides. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the oligonucleotides of the invention (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with an oligonucleotide of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against oligonucleotides of the invention may also be generated by screening expression libraries encoding immunoglobulin genes, or portions thereof, expressed in bacteria with oligonucleotides of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies, or fragments thereof.

Antibodies specifically reactive with the oligonucleotides, or analogues thereof, such as enzyme conjugates or labeled derivatives, may be used to detect UTRs in various biological materials, for example they may be used in any known immunoassays. Examples of such assays are radioimmunoassays, enzyme immunoassays (e.g. ELISA), immunofluorescence, immunoprecipitation, latex agglutination, hemagglutination, and histochemical tests. Thus, the antibodies may be used to detect and quantify UTRs in a sample.

In particular, the antibodies of the invention may be used in immuno-histochemical analyses, for example, at the cellular and subcellular level, to detect UTRs, to localise it to particular cells and tissues and to specific subcellular locations, and to quantitate the level of UTRs.

Cytochemical techniques known in the art for localizing antigens using light and electron microscopy may be used to detect UTRs. Generally, an antibody of the invention may be labelled with a detectable substance and UTRs may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against the oligonucleotides. By way of example, if the antibody having specificity against the oligonucleotide is a rabbit IgG antibody, the second antibody may be goat anti-rabbit gamma-globulin labelled with a detectable substance as described herein.

Where a radioactive label is used as a detectable substance, the UTR may be localized by radioautography. The results of radioautography may be quantitated by determining the density of particles in the radioautographs by various optical methods, or by counting the grains.

Monitoring Cell Status/Therapy

The presence of an oligonucleotide (or UTR) of the present invention may be indicative of the status of the cell. The absence of the UTR may indicate a potential for tumor growth. Assaying a cell for the presence/absence of the UTRs may be useful in monitoring the progression of a cancer therapy. Such assays may be performed using probes or antibodies that bind the UTRs as described in detail above.

Evaluating Substances and Compounds that Modulate Cell Growth

The present invention also includes the use of the oligonucleotides of the invention to evaluate a substance for the ability to interact with, and in particular to bind to oligonucleotides of the invention. Such substances may also modulate cell growth and in particular tumor cell growth, or metastasis in a positive or negative way. Such substances include nucleic acid sequences and proteins. In particular, the substances may be a trans-acting factors (generally proteins) with unique cis-elements in the untranslated regions of the housekeeping genes described herein.

Accordingly, the present invention provides a method for identifying a substance that modulates tumor cell growth or metastasis comprising: (a) reacting a test substance with an oligonucleotide which comprises at least 7 consecutive nucleotides or nucleotide analogues of an untranslated region of a housekeeping gene, under conditions which permit the formation of complexes between the test substance and oligonucleotide, and (b) assaying for complexes, for free substance, for non-complexed oligonucleotide to determine if the substance binds to the oligonucleotide and thereby modulates tumor cell growth or metastasis.

The substance-oligonucleotide complex, free substance or non-complexed proteins may be isolated by conventional isolation techniques, for example, using UV or chemical crosslinking followed by electrophoresis or chromatography of the crosslinked complexes such as mobility gel shifts. To facilitate the assay of the components, antibody against the oligonucleotide or the substance, or labelled oligonucleotide, or a labelled substance may be utilized. The antibodies, oligonucleotide, or substances may be labelled with a detectable substance as described above.

The oligonucleotide, or the substance used in the method of the invention may be insolubilized. For example, the oligonucleotide or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized oligonucleotide or substance may be prepared by reacting the material with a suitable insoluble carrier using known chemical or physical methods, for example, cyanogen bromide coupling.

In an embodiment of the invention, trans-acting proteins are identified by screening cancer cell extracts with the oligonucleotides of the invention. In general, mobility gel shift and UV cross-linking procedures are used (Amara et al, 1993) to identify the presence of a protein and the sequence to which it binds. The binding proteins are purified by methods known in the art and may use for example affinity purification procedures utilizing an oligonucleotide of the present invention which is attached to sepharose beads. Once the proteins are purified and identified, standard techniques can be used to clone the genes for these proteins. Alternatively, cloning of a cDNA encoding an mRNA coding protein could be accomplished by for example screening expression libraries with oligonucleotides of the invention using Northwestern procedures (Qian et al, 1993).

The present invention also includes the use of the oligonucleotides to evaluate compounds for the ability to inhibit or enhance the binding of the oligonucleotides to substances that interact with, or bind to the oligonucleotides.

Accordingly, the present invention provides a method for evaluating a compound for the ability to inhibit or enhance the interaction of an oligonucleotide of the invention with a substance which binds to the oligonucleotide and thereby modulate tumor cell growth or metastasis comprising: (a)

providing a known concentration of the oligonucleotide and a substance which is capable of binding to the oligonucleotide, and a candidate compound under conditions which permit the formation of complexes between the substance and oligonucleotide, and (b) assaying for complexes, for free substance, and/or for non-complexed oligonucleotide to determine if the compound inhibits or enhances the interaction of the substance and oligonucleotide, and thereby modulates tumor cell growth or metastasis.

It will be understood that the agonists and antagonists (i.e. inhibitors and enhancers) that can be assayed using the methods of the invention may act on one or more of the binding sites on the oligonucleotide or substance including agonist binding sites, competitive antagonist binding sites, non-competitive antagonist binding sites or allosteric sites.

The invention also makes it possible to screen for antagonists that inhibit the effects of an agonist of the interaction of the oligonucleotide with a substance which is capable of binding to the oligonucleotide. Thus, the invention may be used to assay for a compound that competes for the same binding site of the oligonucleotide.

The substances and compounds identified by the methods described herein, may be used for modulating the growth of tumor cells, or reducing metastasis. The substances and compounds may be formulated into pharmaceutical compositions as described herein.

The invention also provides methods for examining the function of particular untranslated regions. Cells, tissues, and non-human animals lacking a particular UTR, or part thereof may be developed using recombinant expression vectors of the invention having specific deletion or insertion mutations in the UTR region, or part thereof. A recombinant expression vector may be used to inactivate or alter the endogenous UTR region or part thereof by homologous recombination, and thereby create a UTR deficient or mutant cell, tissue or animal.

Methods and Compositions for Modulating Cell Growth/Metastasis

The oligonucleotides, ribozymes, antisense oligonucleotides, antibodies, and substances and compounds identified using the methods of the invention modulate cell growth and in particular tumor cell growth. Therefore, methods are provided for interfering with cell growth, preferably tumor cell growth comprising contacting tissues or cells with one or more of oligonucleotides, ribozymes, antisense oligonucleotides, and substances and compounds identified using the methods of the invention. Preferably, an oligonucleotide comprising the 3' UTR from ribonucleotide reductase R1 or R2 (SEQ. ID. NO.: 1 or 2) is administered in an amount effective to reduce tumor cell growth. Most preferably, an oligonucleotide as shown in Tables 4 and 5 is administered.

The term "contact" refers to the addition of an oligonucleotide, ribozyme etc, in a liquid carrier to a cell suspension or tissue sample, or to administering the oligonucleotides etc. directly or indirectly to cells or tissues within an animal.

The methods may be used to treat proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, colon cancer, breast cancer, pancreatic cancer, head and neck cancers, and nervous system cancers, benign lesions such as papillomas, arthrosclerosis, angiogenesis, and viral infections, such as HIV infections, hepatitis or herpes infections.

The oligonucleotides, ribozymes, antisense oligonucleotides, and substances and compounds identified using the methods of the invention may also be used to treat drug resistant tumors. Examples of drug resistant tumors are tumors resistant to hydroxyurea; tumors expressing high levels of P-glycoprotein which is known to confer resistance to multiple anticancer drugs such as colchicine, vinblastine and doxorubicin; or, tumors expressing the multi-drug resistance protein as described in R. Deeley et al., Science, 258:1650–1654, 1992.

Particular oligonucleotides of the invention have been found to reduce metastasis. In an embodiment of the invention, a method is provided for reducing metastasis in a subject comprising administering an amount of an oligonucleotide comprising a UTR of ribonucleotide reductase R2, or a part thereof, preferably the 3' UTR of ribonucleotide reductase R2 (SEQ. ID. NO.: 2), or a part thereof, or an oligonucleotide shown in one of SEQ ID. NOs.: 6 to 43. Most preferably the oligonucleotide is one shown in SEQ. ID. NOs.: 6 to 12.

Selected oligonucleotides, ribozymes, antisense oligonucleotides, substances, and compounds may be tested for their ability to modulate cell growth and in particular tumor cell growth, or to reduce metastasis in vitro and in vivo systems as described herein.

For therapeutic applications, the oligonucleotides, ribozymes, antisense oligonucleotides, antibodies, and substances and compounds identified using the methods of the invention may be formulated into pharmaceutical compositions. The pharmaceutical compositions may comprise one or more oligonucleotides, ribozymes, antisense oligonucleotides, antibodies, and substances and compounds identified using the methods of the invention for administration to subjects in a biologically compatible form suitable for administration to a subject. The compositions of the invention can be intended for administration to humans and various other mammals, such as ovines, bovines, equines, swine, canines, and felines.

The pharmaceutical compositions of the invention may be administered in different ways depending upon whether local or systemic treatment is desired, and upon the area to be treated. The compositions can be administered orally, subcutaneously or parenterally including intravenous, intraarterial, intramuscular, intraperitoneally, and intranasal administration as well as intrathecal and infusion techniques as required by the malignant cells being treated. For delivery within the CNS intrathecal delivery can be used with for example an Ommaya reservoir or other methods known in the art. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids (e.g. Lipofectin, Life Technologies) may also be included in the composition to facilitate oligonucleotide uptake. Implants of the compounds are also useful. In general the pharmaceutical compositions are sterile.

The oligonucleotides, antisense oligonucleotides, and ribozymes of the invention may be delivered using viral or non-viral vectors. Sequences may be incorporated into cassettes or constructs such that an oligonucleotide, ribozyme, or antisense oligonucleotide of the invention is expressed in a cell. Generally the construct contains the proper transcriptional control region to allow the oligonucleotide or antisense oligonucleotide to be transcribed in the cell.

Therefore, the invention provides vectors comprising a transcription control sequence operatively linked to a sequence which encodes an oligonucleotide ribozyme, or antisense oligonucleotide of the invention. The present invention further provides host cells, selected from suitable eucaryotic and procaryotic cells, which are transformed with these vectors. Such transformed cells allow the study of the function and the regulation of malignancy and the treatments of the present invention.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), Vectors: *A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors.

Introduction of nucleic acids by infection offers several advantages. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of a DNA viral vector for introducing and expressing the UTR mRNA R1 and/or R2 sequence is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells including, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include; for example, promoter and regulatory elements that are specific for the desired cell type.

Recombinant viral vectors are another example of vectors useful for in vivo introduction of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

A vector to be used in the methods of the invention may be selected depending on the desired cell type to be targeted. For example, if breast cancer is to be treated, then a vector specific for such epithelial cells should be used. Similarly, if cells of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The pharmaceutical compositions and vectors of the invention may be administered in combination with other drugs or singly, consistent with good medical practice such as cytotoxic agents, immunotoxins, alkylating agents, antimetabolites, antitumor antibiotics and other anti-cancer drugs and treatment modalities that are known in the art.

Dosing of the oligonucleotides, ribozymes, antisense oligonucleotides, antibodies, substances and compounds will depend on the severity and responsiveness of the condition to be treated with a course of treatment lasting from several days to several months or until diminution of the disease is achieved. Optimal dosing schedules may be calculated using measurements of drug accumulation in the body. Persons of ordinary skill in the art can readily determine optimum dosages, dosing methodologies, and repetition rates. Optimum dosages may vary depending on the relative potency of individual oligonucleotides, and can generally be determined based on $ED_{50}s$ in in vitro and in vivo animal studies.

The following non-limiting examples are illustrative of the present invention.

EXAMPLES

General Methods:

GENERAL METHODS IN MOLECULAR BIOLOGY: Standard molecular biology techniques known in the art and not specifically described were generally followed as in Sambrook et al., *Molecular Cloning: A Laboratory Manual*, Cold Springs Harbor Laboratory, New York (1989, 1992); in Ausubel et al., *Current Protocols in Molecular Biology*, John Wiley and Sons, Baltimore, Md. (1989); and in Perbal, *A Practical Guide to Molecular Cloning*, John Wiley & Sons, New York (1988). Polymerase chain reaction (PCR) was carried out generally as in *PCR Protocols: A Guide To Methods And Applications*, Academic Press, San Diego, Calif. (1990).

Vectors can be constructed for the present invention by those skilled in the art and should contain all expression elements necessary to achieve the desired transcription of the sequences. The expression elements can be selected to allow expression only in the cell being targeted. Other beneficial characteristics can also be contained within the vectors such as mechanisms for recovery of the nucleic acids in a different form. One of ordinary skill in the art will know which expression elements are compatible with a particular cell type. The vectors can be introduced into cells or tissues by any one of a variety of known methods within the art as described herein above.

GENERAL METHODS IN IMMUNOLOGY: Standard methods in immunology known in the art and not specifically described were generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

ASSAYS FOR TUMORIGENICITY AND METASTASIS: Malignancy potential was determined as reported previously [Wright, 1989a; Egan et al., 1987a, 1987b; Damen et al., 1989; Taylor et al., 1992; Stokoe et al., 1994]. Six to eight week old C3H/HeN syngeneic mice (Charles River, Quebec) were used to evaluate tumorigenic and metastatic potential of the cells. Cells were prepared from subconfluent, logarithmically growing cultures, collected by gentle treatment with trypsin/EDTA solution and adjusted to appropriate concentration in a balanced salt solution.

For the tumorigenicity (tumor latency) assay, $1\times10^5$ cells in a 0.1 ml volume were injected subcutaneously into the back of mice and the time required to form a tumor (2×2 mm) detectable by palpation was recorded. The growth of tumors was also evaluated by measuring tumor diameters, and estimating tumor base area each day following tumor appearance [Damen et al., 1989]. Tumor size was determined by multiplying the dimensions of the cross-section of the tumor. Tumors were removed from the mice and tumor weight was recorded 21 days later. In the case of no tumor formation, mice were kept for 2 months after injection and then sacrificed.

For experimental metastasis assays (determination of metastatic potential), $1\times10^5$ cells in a 0.2 ml volume were injected into the tail veins of 6–8 week old C3H/HeN syngeneic mice and an estimate of the number of lung tumors was made 21 days later. The mice were sacrificed, and the lungs were stained by injecting Bouin's solution {picric acid, formaldehyde, acetic acid (15:5:1)} intratracheally [Egan et al., 1987b; Damen et al., 1989]. Pulmonary tumors were counted with the aid of a dissecting microscope. To confirm that equal numbers of test and control cells were injected, duplicate culture plates containing growth medium were inoculated with 100 cells per plate. After 10 days in culture, plates were stained with methylene blue and colonies were scored.

Example 1

Neoplastic transformation is a multi-stage process that usually proceeds through the accumulation of numerous genetic alterations [Nowell, 1986; Wright et al., 1993]. Activation of specific oncogenes and inactivation of tumor suppressor genes play important roles in this mechanism. In previous studies, Applicants have shown that mouse $10T_{1/2}$ fibroblasts transfected with a combination of T24-H-ras, human c-myc and the proline 193 mutant form of p53 exhibit tumorigenic and metastatic properties in syngeneic mice [Taylor et al., 1992; Huang et al., 1995b]. RMP-6 is one of these highly malignant cell lines that has been characterized in these earlier studies. Applicants tested whether expression of these RNA regions in malignant cells would modify malignancy-related characteristics using the RMP-6 cell line.

In preparation for these experiments, RMP-6 cells were transfected by the calcium phosphate precipitation procedure with expression plasmids containing the R1 3' UTR (SEQ ID No:1), the R2 3' UTR (SEQ ID No:2) or with the empty vector as a control, to yield the cell lines RMPM1U, RMPM2U and RMP-VC, respectively. RMP-6 cells were also transfected by electroporation with the same plasmid constructs to produce the cell lines eRMPM1U (R1 3' UTR), eRMPM2U (R2 3' UTR) and eRMP-VC (empty vector) (FIG. 1). Cells transfected by either calcium phosphate precipitation or by electroporation express the transfected 3' UTRs. In addition, an 831 base fragment encoded by chlamydial DNA was expressed in cells transfected with pHNC0.8. The plasmid constructs also contain the coding region for the luciferase enzyme, and as expected all transfected cell lines contained luciferase activity.

Materials and Methods

Construction of expression plasmids for the 3' UTRs of ribonucleotide reductase: A 1854 bp fragment of a recombinant hygromycin gene which contained a mammalian thymidine kinase promoter, the coding region of the hygromycin gene, and a thymidine kinase polyadenylation signal was PCR-amplified from the plasmid pEBVHis (Invitrogen Corp., San Diego, Calif.), and inserted into the Bst1107I site of the mammalian expression plasmid pcDNA3 (Invitrogen Corp.), to give the plasmid pHN. A 1696 base pair (bp) fragment which covered the 1650 bp coding region and 46 bp 3' UTR of firefly luciferase cDNA was amplified from pMAMneo-luc (Clontech, Palo Alto, Calif.), and inserted into the HindIII and KpnI-restricted pHN. Into the KpnI and XhoI sites of the resulting plasmid were inserted the 446 bp fragment of R1 3' UTR, and the 876 bp fragment of the R2 3 UTR, amplified from the pCD-R1 and pCD-R2 plasmids [Amara et al., 1994; Chen et al., 1993; Thelander and Berg, 1986], to produce the R1 and R2 3' UTR expression plasmids, pHNM1U and pHNM2U, respectively.

A control expression plasmid, pHNC0.8 was also constructed by inserting a 831 bp fragment of *Chlamydia trachomatis* genomic DNA into the BamH1 and XhoI sites of the same vector. The 831 bp chlamydial fragment is a 3'-portion of an open reading frame encoding a thymidylate synthase [Fan et al., 1996C]. In pHNM1U, pHNM2U and pHNC0.8, the synthesis of a recombinant luciferase mRNA, which contains (from 5'→3') the luciferase coding region, 46 bases of luciferase 3' UTR plus the full length 3' UTR of R1, R2 or the chlamydial sequence is under the control of a cytomagalovirus promoter.

In addition, the cDNA fragments for R1 or R2 3' UTRs were directionally cloned into KpnI/XhoI cut pcDNA3 plasmid to yield expression vectors pD3M1U and pD3M2U, respectively. In these latter two vectors, full length R1 or R2 3' UTR without an upstream luciferase coding fragment is also under the control of a cytomegalovirus promoter. The orientation of the inserts in all the recombinant plasmids was confirmed by sequence analysis using a sequencing kit (Gibco BRL, Burlington, Ontario).

Transfection of plasmid DNA into cells: Expression plasmid DNA was introduced into human Hela cells by calcium phosphate precipitation, and into RMP-6 cells by calcium phosphate precipitation or electroporation [Taylor et al., 1992; Huang et al., 1995b]. For calcium phosphate precipitation, $5 \times 10^5$ cells were seeded into 10 cm cell culture dishes containing 10 ml of α-minimal essential medium (Gibco) supplemented with 10% serum (Fetal Clone III, Hyclone, UT). After about 16 hours of culture at 37° C. in the presence of 5% $CO_2$, the medium was changed and cells were cultured a further 3 hours. Twenty µg of DNA was used for transfection of each dish of cells; the DNA-phosphate precipitates were prepared as previously described [Taylor et al., 1992; Huang and Wright, 1994]. After 16 hours of cell culture, the precipitates were removed and cells were washed twice with phosphate buffered saline, pH 7.2 and fresh medium was added for overnight culture. RMP-6 cells were then cultured in medium containing 400 µg/ml hygromycin (Boehringer-Mannheim, Mannheim, Germany), and Hela cells were cultured in medium containing 800 µ/ml geneticin (Gibco). Selected stable transfectant colonies (more than 500 in total) were identified, removed with trypsin solution, pooled and cultured in the selective medium for another 10 days to ensure that they were drug resistant [Huang and Wright, 1994].

For electroporation, the expression plasmids were linearized with Ssp1, extracted with phenol:chloroform, precipitated with ethanol and redissolved in serum-free medium containing 10 mM Hepes (pH 7.2). Logarithmically growing cells were removed with trypsin solution, and washed twice with 10 mM Hepes (pH 7.2). An electroporation mixture was prepared in an electroporation cuvette and contained, in a total volume of 400 µl, $7 \times 10^6$ cells 20 µg of Ssp1-digested plasmid DNA. The electroporation was achieved by using a Gene Pulser (Bio-Rad, Mississauga, ON) with settings at 960 µF and 250 V. After 5 minutes incubation at room temperature, the cells were transferred into a 10 cm culture dish containing 15 ml of growth medium. After overnight culture, hygromycin was used to select for stable transfectants [Huang and Wright, 1994].

Reverse transcriptase PCR (RT-PCR): Total cellular RNA was extracted from approximately 70% confluent cultures by using a Micro RNA Isolation Kit as instructed by the manufacturer (Strategene, La Jolla, Calif.). An Sp6 primer (5' GGATTTAGGTGACACTATAG3', SEQ ID No:3) located 20 bp downstream of the XhoI-cutting site of the vector (where the R1 or R2 3' UTRs were cloned) was used for reverse transcription from the recombinant mRNAs containing the UTRs. A second primer (5' TGAGAAAAGCGGGGCCTG3', SEQ ID No:4), which is the first 18 bp of the R1 3' UTR, and a third primer (5' TAAGTAACTGATCGTGTGCTC3', SEQ ID No:5), which represents the first 21 bp of the R2 3' UTR was used in combination with the Sp6 primer to amplify the recombinant cDNAs. A chlamydial DNA primer (5'TTAAGACTTTT-TACGCGATTC3', SEQ ID No:50) was used together with the Sp6 primer to detect expression of the bacterial fragment in pHNC0.8 transfected cells.

An EZ rTth RNA PCR Kit (Perkin Elmer, Branchburg, N.J.) was used for the RT-PCR. Briefly, an RT-PCR reaction contained, in a total volume of 50 µl, 1×EZ buffer (Perkin Elmer), 300 µM of each deoxyribonucleoside triphosphate, 2.5 mM $Mn(OAc)_2$, 100 ng of RNA template, 0.45 µM each of two primers and 5.0 units of rTth Polymerase. To ensure that the final amplification product was initially amplified from RNA instead of a possible DNA contaminant in the RNA samples, a parallel reaction was carried out, in which 1 µg of DNase-free RNase A was added into, and incubated with, the reaction mixture for 5 minutes before the addition of the polymerase.

The synthesis of cDNA from template mRNA and later amplification of the cDNA was achieved by incubation at 60° C. for 60 minutes, then 94° C. for 2 minutes followed by 40 temperature cycles of 20 seconds of denaturing at 94° C., 90 seconds of annealing and extension at 60° C., and a final 7 minutes incubation at 60° C. At the end of the reaction, 10 µl of sample was analyzed by electrophoresis on 1% agarose gel.

Tumorigenicity and metastasis analysis: Malignant potential was determined as described herein above.

Results

Figure 2:
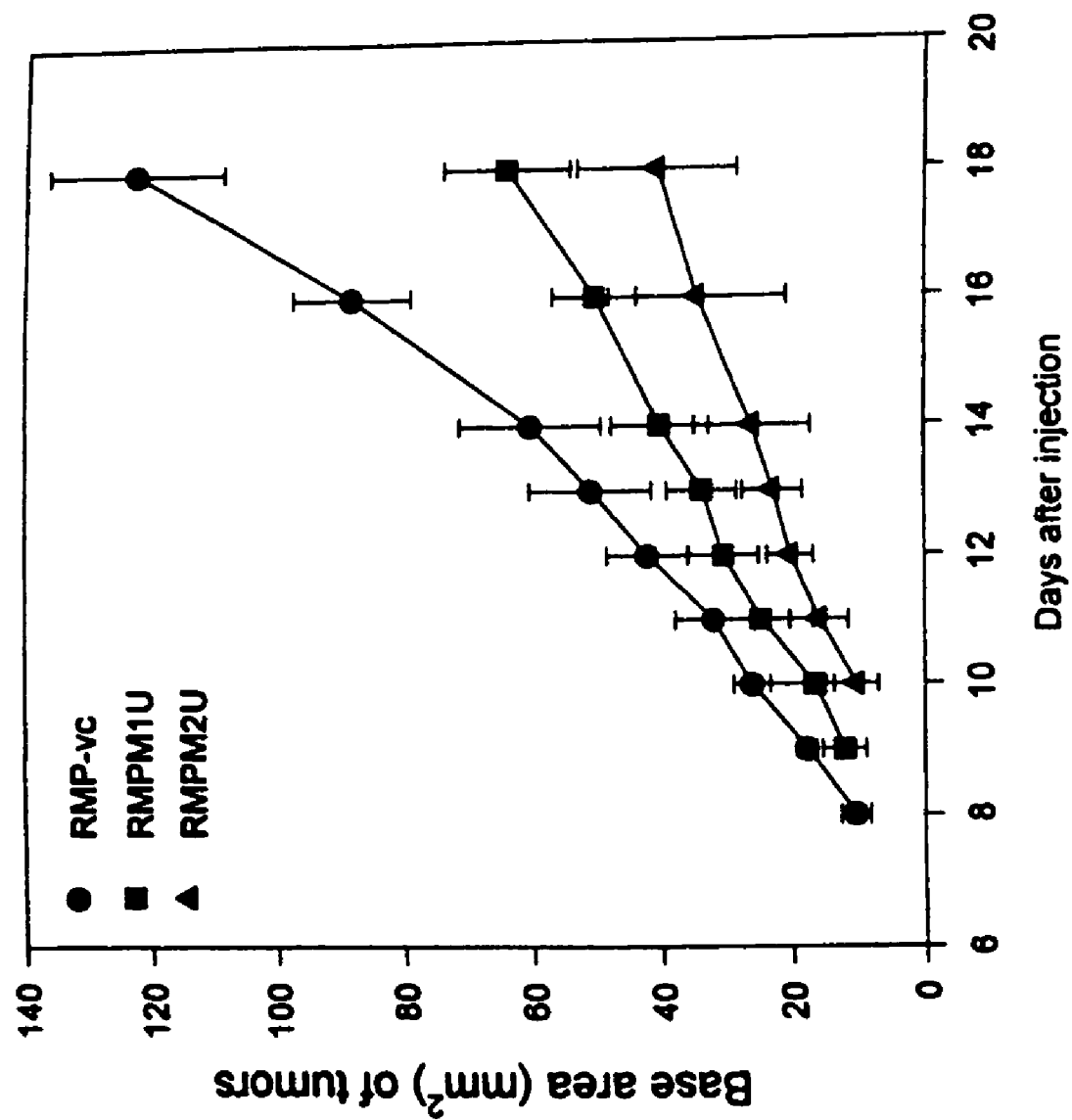
FIG. 2 is a graph showing the growth of subcutaneous tumors in syngeneic mice (Example 1).

To evaluate the possibility that expression of the ribonucleotide reductase 3' UTRs affect tumorigenicity, syngeneic mice were injected subcutaneously with the transfected cell lines and tumor weight and growth was determined. Metastatic potential in syngeneic mice was estimated by a tail vein experimental lung metastasis assay. Cells expressing R1 and R2 3' UTRs produced subcutaneous tumors that were significantly reduced in weight when compared to results obtained with control cells that were transfected with the empty vector (Table 1). Similar results were obtained with cells that were transfected with the calcium phosphate precipitation procedure and with cells that were transfected by electroporation (Table 1). In keeping with these observations, FIG. 2 shows that the growth of tumor cells transfected with the 3 UTRs from R1 or R2 mRNAs was significantly slower than the growth of cells transfected with the vector alone.

To further examine specificity in the reduced tumorigenicity observed with cells expressing R1 or R2 3'UTRs, the tumorigenicity of cells transfected with pHNC0.8 which express 831 bases of chlamydial sequence were compared with cells transfected with the empty vector. There was no significant difference between the two cell populations as determined by estimating tumor weight (Table 1) or tumor latency (data not shown). Cancer mortality is primarily caused by the ability of tumor cells to metastasize [Nowell, 1986]. Interestingly, cells expressing the R2 3' UTR (SEQ ID No:2) exhibited a significantly reduced ability to disseminate to the lungs of syngeneic animals as compared to control cells transfected with the vector alone (Table 1). Expression of the R1 3' UTR (SEQ ID No:1) did not significantly alter metastatic potential when compared to the control population (Table 1), indicating that expression of the R1 3' UTR suppresses tumorigenic but not metastatic potential.

The R2 3'UTR (SEQ ID No:2) exhibited both tumorigenic and metastatic suppressive effects, and as was observed in the tumorigenic studies, the metastatic properties of the transfectants were essentially independent of the method that was used to perform the transfections.

To determine whether or not the mouse R1 and R2 3'UTRs can suppress human tumor cell potential, Hela cells were transfected by calcium phosphate precipitation with the expression vectors containing either the R1 3'UTR (Hela M1U cells) or the R2 3'UTR (Hela M2U cells). As was observed with mouse tumor cells, growth of Hela M1U and Hela M2U cells was significantly reduced when compared to control Hela cells containing the expression vector without R1 or R2 3'UTR sequences (Table 2).

Example 2

Further Results Using the R1 and R2 Untranslated Regions

Using the methods herein above, oligonucleotides of R1 and R2 3'-UTR mRNA segments as set forth in Tables 4 and 5 were screened for tumor cell cytotoxicity in relative colony forming efficiency experiments [Huang and Wright, 1994]. Hela 53 and Hela 1 mM tumor cells were used as well as a variety of human cancer cell lines as noted in Tables 6 and 7. The cells were cultured for 24 hours at 37° C. in growth medium with 10% fetal bovine serum. The cells were washed in 5 ml phosphate buffered saline, pH 7.2, once prior to lipofectin +/−oligonucleotide treatment.

The oligonucleotides being tested were added to cell cultures in the presence of 2.5 µg of DOTMA/DOPE (Lipofectin; Life Technologies, Inc.) for four hours. The oligonucleotide was tested at 0.2 µM unless otherwise indicated. Controls were the cultures treated with lipofectin but without the oligonucleotide. After 4 hours the medium containing the oligonucleotide was removed and washed with 5 ml of growth medium. The cells were then cultured in growth medium containing 10% fetal bovine serum for seven to ten days. In some experiments cell aliquotes were removed from the culture and viability was determined using trypan blue exclusion test [Phillips, 1973]. Results were analyzed as percent of surviving cells compared to control cells.

A short oligodeoxyribonucleotide phosphorothioate sequence, Sen-II-2229B-20 (SEQ ID No:7; Table 5) was used to inhibit the proliferation of human tumor cells (Hela) in relative colony forming efficiency experiments. Hela S3 cells (American Type Culture Collection, Rockville, Md., U.S.; ATCC) and a Hela cell line (Hela 1 mM) previously selected for resistance to the antitumor agent hydroxyurea [Wright et al., 1987] were used in these experiments (Table 6). Clearly, Sen-II-2229B-20 is a very effective inhibitor of human tumor cell colony forming ability. It is also effective in inhibiting the proliferation of human tumor cells that exhibit resistance to hydroxyurea, a chemotherapeutic compound of clinical significance.

Sen-II-2229B-20 (SEQ ID No:7) and Sen-II-2229A-20 (SEQ ID No:6) are alternative sequences, with 2229A chosen from the version of R2 in GENBANK (submitted by Pavloff) and 2229B chosen from the version published by Pavloff et al. The two sequences provided similar results.

Sen-II-2229B-20 (SEQ ID No:7) and six other 20-mer oligodeoxyribonucleotide sequences (SEQ ID Nos:6,8–12) corresponding to sequence segments (fragments) of the 3'-UTR of R2 and one corresponding to the 3'-UTR of R1 (SEQ ID No:45; Table 4), were tested in relative colony forming efficiency experiments to determine inhibitory effects using a variety of human cancer cells. The results showing estimated percent inhibition of relative colony forming abilities of these various oligonucleotides are provided in Table 7. Clearly, all the compounds were effective antitumor agents against human cancer cells derived from the bladder, colon, lung, breast and pancreas.

Furthermore, analysis of Hela S3 and WI38 (normal strain) cell viability by the trypan blue exclusion test three days after oligonucleotide exposure indicated that Hela S3 tumor cells were approximately three times more sensitive to the cytotoxic effects of Sen-II-2229B-20 oligonucleotide than normal non-tumorigenic WI38 cells averaged over 4–8 determinations.

Throughout this application, various publications, including United States patents and published patent applications are referenced by author and year or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

Throughout this application, various publications, including United States patents and published patent applications are referenced by author and year or number. Full citations for the publications are listed below. The disclosures of these publications and patents in their entireties are hereby incorporated by reference into this application in order to more fully describe the state of the art to which this invention pertains.

Detailed legends for FIGS. 1 and 2 are also provided in the following pages.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

TUMORIGENICITY AND METASTATIC POTENTIAL OF RMP-6 TRANSFECTED CELL LINES.

| Cell Line | Transfected R1 or R2 mRNA 3' UTR | Tumorigenicity: Subcutaneous Tumor Weight (g) (mean ± SE)[1] | Experimental Lung Metastases: Number (mean ± SE)[2] |
|---|---|---|---|
| RMP-VC | — | 1.05 ± 0.22 (n = 10)[3] | 17.3 ± 6.8 (n = 10)[3] |
| RMPM1U | R1 | 0.58 ± 0.21 (n = 10) | 20.0 ± 9.7 (n = 10) |
| RMPM2U | R2 | 0.13 ± 0.14 (n = 10) | 6.4 ± 5.4 (n = 10) |
| eRMP-VC | — | 1.21 ± 0.14 (n = 5) | 20.5 ± 6.7 (n = 5) |
| eRMPM1U | R1 | 0.3 ± 0.31 (n = 5) | 16.1 ± 6.1 (n = 5) |
| eRMPM2U | R2 | 0.18 ± 0.11 (n = 5) | 9.2 ± 2.3 (n = 5) |

[1] Using Student's t-test the differences in the tumorigenicity results obtained with RMPM1U and RMPM2U cells were found to be statistically significant, when compared to the results obtained with RMP-VC cells, with p values of <0.02 and <0.001, respectively. Similarly, the tumorigenicity results obtained with eRMPM1U and eRMPM2U cells were significantly different from the results obtained with eRMP-VC cells, with p values of <0.01 in both cases.

[2] Using Student's t-test the numbers for experimental metastases obtained with RMPM1U and eRMPM1U cells were not found to be statistically different from the results obtained with the RMP-VC or the eRMP-VC control cell populations, respectively. However, the numbers for experimental metastases observed with RMPM2U and eRMPM2U cells were significantly different when compared to the observations obtained with RMP-VC or eRMP-VC cells, with p values of <0.02 in both cases.

[3] The number of animals/experiment is shown in ( ).

[4] As an added control for specificity the tumorigenicity of RMP-VC cells was compared to cells transfected with pHNC0.8 to produce the RMPC0.8 cell line, which expresses a 831 base chlamydial sequence (see FIG. 1). No significant difference was observed; tumor weights of 1.19 ± 0.26 (n = 8) and 1.24 ± 0.33 (n = 7) for RMP-VC and RMPC0.8 cells, respectively (p value >0.5).

TABLE 2

TUMORIGENIC POTENTIAL OF HUMAN HELA TRANSFECTED CELL LINES

| Cell Line | Transfected R1 or R2 mRNA 3'UTR | Tumorigenicity Subcutaneous Tumor Weight (g), mean SE[1] |
|---|---|---|
| Hela-VC | — | 0.177 ± 0.026 |
| Hela M1U | R1 | 0.055 ± 0.016 |
| Hela M2U | R2 | 0.072 ± 0.033 |

[1] Using Student's t-test the differences in the tumorigenicity results obtained with Hela M1U and Hela M2U cells were found to be statistically significant, when compared to the results obtained with Hela-VC cells, with p values of <0.01 and <0.05, respectively. The number of animals/experiment was 5.

TABLE 3

PARTIAL LISTING OF HOUSEKEEPING GENES
Genes indicated by an * have been observed to be altered in cancer cells.

a) Nucleic acid metabolism
  Ribonucleotide reductase*
  Carbamoyl-phosphate synthetase II*
  Aspartate carbamoyltransferase*
  Dihydroorotate*
  Dihyrofolate reductase*
  CTP synthetase*
  Thymidylate synthetane*
  Deoxycytidylate deaminase*
  Uridine-cytidine kinase*
  Deoxycytidine kinase*

TABLE 3-continued

PARTIAL LISTING OF HOUSEKEEPING GENES
Genes indicated by an * have been observed to be altered in cancer cells.

Thymidine kinase*
  DNA polymerase*
  DNA nucleotidyltransferases*
  RNA polymerases*
  tRNA methylase*
  Dihydrouacil dehydrogenase*
  Formylglycinamidine ribonucleotide synthetase*
  IMP dehydrogenase*
  GMP synthetase*
  AMP deaminase*
  Adenylate kinase*
b) Carbohydrate metabolism
  Hexokinase*
  Phosphofructokinase*
  Pyruvate kinase*
  Glucose-6-phosphatase*
  Fructose-1,6-diphosphatase*
  Phosphoenolpyruvate carboxykinase*
  Pyruvate carboxylase*
  Fructokinase*
  Glucokinase*
  Thiokinase*
  Aldolase*
  glyceraldehyde-phosphate dehydrogenase*
c) Protein and amino acid metabolism
  Glutamate dehydrogenase*
  Glutamate-oxaloacetate transaminase*
  Tryptophan pyrrolate*
  Glutaminase*
  5-Hydroxytryptophan decarboxylase
d) Lipid metabolism
  Acetyl-CoA carboxylase
  α-Glycerophosphate dehydrogenase*
  Hydroxymethylglutaryl-CoA synthase*
e) Other metabolic activities
  Ornithine decarboxylase*
  Ornithine carbamoyltransferase*
  cAMP phosphodiesterase*
  Adenylate cyclase*
  S-Adenosylmethionine synthetase*
  Citrate synthase
  Aconitase
  Isocitrate dehyrogenase
  Succinyl-CoA srrythase
  Succinate Dehyrogenase
  Fumerase
  NADH dehydrogenase

TABLE 4

R1 UTR Sequence Segments Designed
SEQ ID No: To Inhibit Tumor Cell Growth

| SEQ ID No | Name | Sequence | Tm | dG | D | H | A |
|---|---|---|---|---|---|---|---|
| SEQ ID No:44 | Sen-I-2627-20 | AGTGGGTTTGCTTGAGGTGG | 53.9 | −39.1 | ✓ | ✓ | ✓ |
| SEQ ID No:45 | Sen-I-2650-20 | GGCTTTGCTGGACCCTGTTG | 56.8 | −40.9 | ✓ | ✓ | ✓ |
| SEQ ID No:46 | Sen-I-2767-20 | AAAAAAAGAAAAAAAAAACG | 44.0 | −36.6 | ✓ | ✓ | ✓ |
| SEQ ID No:47 | Sen-I-2804-20 | AGTAGAAGTTTTAGGAATGC | 40.1 | −33.1 | ✓ | ✓ | ✓ |
| SEQ ID No:48 | Sen-I-2863-20 | GTTTCATCACCCATTTAGCA | 47.5 | −35.8 | ✓ | ✓ | ✓ |
| SEQ ID No:49 | Sen-I-2923-20 | TTTACTGCTTTGACTGGTGG | 47.8 | −35.7 | ✓ | ✓ | ✓ |

TABLE 5

R2 UTR Sequence Segments Designed
To Inhibit Tumor Cell Growth

| SEQ ID No: | Name* | Sequence 5'–3' | $Tm^1$ °C. | $dG^2$ KCal/mol | $D^3$ | $H^4$ | $A^5$ |
|---|---|---|---|---|---|---|---|
| SEQ ID No:6 | Sen-II-2229A-20 | GAGTTTTCATATGTGGGAGC | 46.1 | −35.2 | X | ✓ | ✓ |
| SEQ ID No:7 | Sen-II-2229B-20 | GAGTTTTCTCATATGTGGGA | 43.7 | −33.7 | X | X | ✓ |
| SEQ ID No:8 | Sen-II-1364-20 | AATGAACTGAAGATGTGCCC | 48.9 | −36.2 | ✓ | ✓ | ✓ |
| SEQ ID No:9 | Sen-II-2083-20 | AGGAATCTCTCAGGGCAAGG | 52.3 | −39.0 | ✓ | ✓ | ✓ |
| SEQ ID No:10 | Sen-II-1791-20 | GCTTGATTTATTTGGTTTCT | 43.4 | −34.9 | ✓ | ✓ | X |
| SEQ ID No:11 | Sen-II-1992-20 | GCCAGATAGAAGACAGGTTG | 46.2 | −35.0 | ✓ | ✓ | ✓ |
| SEQ ID No:12 | Sen-II-2019-20 | ATCCTGTGGCTTGTGTAGTG | 47.2 | −34.7 | ✓ | ✓ | ✓ |
| SEQ ID No:13 | Sen-II-1396-20 | TTTTTTTTTTCCATCTCATA | 42.3 | −34.3 | ✓ | ✓ | ✓ |
| SEQ ID No:14 | Sen-II-1561-20 | CTGGCTGGCTGTGACTTACC | 52.2 | −37.8 | ✓ | ✓ | ✓ |
| SEQ ID No:15 | Sen-II-1772-20 | ACTCACGGCGGCGATAATAG | 54.4 | −40.8 | ✓ | ✓ | ✓ |
| SEQ ID No:16 | Sen-II-1818-20 | ATACATTCTCCTGACCACTA | 40.5 | −32.1 | ✓ | ✓ | ✓ |
| SEQ ID No:17 | Sen-II-2007-20 | GGTTGTGTTTTTATCCTGTG | 44.5 | −34.1 | ✓ | ✓ | ✓ |
| SEQ ID No:18 | Sen-II-2013-20 | GTTTTTATCCTGTGGCTTGT | 46.1 | −35.6 | ✓ | ✓ | ✓ |
| SEQ ID No:19 | Sen-II-2024-20 | GTGGCTTGTGTAGTGTCCTG | 47.6 | −34.5 | ✓ | ✓ | ✓ |
| SEQ ID No:20 | Sen-II-2060-20 | CTGAGTAGAGTGTTGTGGGA | 44.3 | −33.0 | ✓ | ✓ | ✓ |
| SEQ ID No:21 | Sen-II-2069-20 | GTGTTGTGGGATAAAGGAAT | 45.5 | −35.2 | ✓ | ✓ | ✓ |
| SEQ ID No:22 | Sen-II-2180-20 | TCTCACTGTATTTTCCTCAA | 41.8 | −32.6 | ✓ | ✓ | ✓ |
| SEQ ID No:23 | Sen-II-2373-20 | GGTGTAAGTAGGTTGTGTGA | 41.7 | −32.0 | ✓ | ✓ | ✓ |
| SEQ ID No:24 | Sen-II-2079-20 | ATAAAGGAATCTCTCAGGGC | 46.9 | −36.7 | ✓ | ✓ | X |
| SEQ ID No:25 | Sen-II-1771-20 | TACTCACGGCGGCGATAATA | 53.4 | −40.1 | ✓ | ✓ | X |
| SEQ ID No:26 | Sen-II-1581-20 | ATAGCAGTGACAATGGCAGT | 47.0 | −34.9 | ✓ | ✓ | ✓ |
| SEQ ID No:27 | Sen-II-1575-20 | CTTACCATAGCAGTGACAAT | 41.6 | −32.7 | ✓ | ✓ | X |
| SEQ ID No:28 | Sen-II-1499-29 | GCTACCTCACAACCAGTCCT | 48.1 | −35.7 | ✓ | ✓ | X |
| SEQ ID No:29 | Sen-II-1386-20 | ACTTGGCTGATTTTTTTTTT | 45.7 | −36.6 | ✓ | ✓ | X |
| SEQ ID No:30 | Sen-II-1560-21 | CCTGGCTGGCTGTGACTTACC | 56.0 | −40.9 | ✓ | ✓ | ✓ |
| SEQ ID No:31 | Sen-II-1818-21 | ATACATTCTCCTGACCACTAA | 43.0 | −34.0 | ✓ | ✓ | X |
| SEQ ID No:32 | Sen-II-1536-22 | GTAGTATCACCTTTTGCCAGAA | 48.3 | −37.8 | ✓ | ✓ | X |
| SEQ ID No:33 | Sen-II-1989-23 | GGTGCCAGATAGAAGACAGGTTG | 54.4 | −41.3 | ✓ | ✓ | ✓ |
| SEQ ID No:34 | Sen-II-1361-24 | CTAAATGAACTGAAGATGTGCCCT | 53.5 | −42.2 | ✓ | ✓ | X |
| SEQ ID No:35 | Sen-II-1791-24 | GCTTGATTTATTTGGTTTCTACAC | 49.2 | −40.3 | ✓ | ✓ | X |
| SEQ ID No:36 | Sen-II-2079-25 | ATAAAGGAATCTCTCAGGGCAAGGA | 57.6 | −46.8 | ✓ | ✓ | ✓ |
| SEQ ID No:37 | Sen-II-2432-25 | ATTTTTTATTATCTATGTTCTTCTA | 41.8 | −37.6 | ✓ | ✓ | X |
| SEQ ID No:38 | Sen-II-1381-27 | CCCTTACTTGGCTGATTTTTTTTTTCC | 59.6 | −51.9 | ✓ | ✓ | X |
| SEQ ID No:39 | Sen-II-2060-29 | CTGAGTAGAGTGTTGTGGGATAAAGGAAT | 57.6 | −48.9 | ✓ | ✓ | ✓ |
| SEQ ID No:40 | Sen-II-2162-38 | AAGCCGTTTCATTTTATTTCTCACTGTATTTTCCTCAA | 66.8 | −67.9 | ✓ | ✓ | ✓ |
| SEQ ID No:41 | Sen-II-2362-34 | TAGTTTTGTTTGGTGTAAGTAGGTTGTGTGAGTT | 60.8 | −55.2 | ✓ | ✓ | ✓ |
| SEQ ID No:42 | Sen-II-2463-37 | ACCTGTAGTTCATAAAAAAAAAAAAAAAAAAAAAAAAA | 60.7 | −64.5 | ✓ | ✓ | X |
| SEQ ID No:43 | Sen-II-2007-39 | GGTTGTGTTTTTATCCTGTGGCTTGTGTAGTGTCCTGGG | 72.9 | −71.6 | ✓ | ✓ | X |

FOOTNOTES FOR TABLES 4 AND 5
*Name includes the following:
Sen = sense
I = R1
or
II = R2
The first number is the first nucleotide position in the R2 mRNA sequence.
The second number is the length of the sequence segment.
[1]Tm ° C. = Melting temperature of oligonucleotide duplex formed
[2]dG = Free energy values for oligonucleotide-complement dimer formation
[3]D = Estimate of potential dimer former (✓ = no potential; X = some potential)
[4]H = Estimate for potential self-complementary interations (✓ = no potential; X = some potential)
[5]A = Estimate for potential to bind to sequences in the R1 or R2 messages (✓ = no potential; X = some potential)

The estimates were determined by using the computer modeling program OLIGO Primer Analysis Software, Version 3.4 (distributed by National Biosciences). The program allows the determination of a qualitative estimation of these three parameters and indicates "no potential" or "some potential" or "essentially complete potential". Segments were generally selected that had estimates of no potential in all three parameters. However, several segments as shown in Table 5 had parameters that were in the "some potential" category and were still effective having a reduced (some) potential. A balance of the parameters is used in the selection.

TABLE 6

DOSE DEPENDENT REDUCTION OF COLONY FORMING EFFICIENCY FOLLOWING TREATMENT WITH R2 UTR Sen-II-2229b-20

| | Concentration | % Inhib. |
|---|---|---|
| CELL LINE: Hela S3 | | |
| Exp. 1 | 0 | — |
| | 0.05 µM | 50% |
| | 0.10 µM | 55% |
| | 0.20 µM | 88% |
| Exp. 2 | 0 | |
| | 0.02 µM | |
| | 0.05 µM | 20% |
| | 0.10 µM | 48% |
| | 0.2 µM | 80% |
| CELL LINE: Hela 1 mM | | |
| | 0 | — |
| | 0.05 µM | — |
| | 0.10 µM | 50% |
| | 0.20 µM | 85% |

TABLE 7

Reduced Relative Colony Forming Efficiency Following Treatment with 0.2 µM of Various Oligodeoxyribonucleotide Phosphorothioates Corresponding to the Untranslated Regions of R1 or R2 mRNAs*

| Cell Lines/ Oligos | Sen-II-1364-20 | Sen-II-1791-20 | Sen-II-1992-20 | Sen-II-2019-20 | Sen-II-2083-20 | Sen-II-2229A-20 | Sen-II-2229B-20 | Sen-I-2650-20 |
|---|---|---|---|---|---|---|---|---|
| T24 Human Bladder Carcinoma | 60% | 50% | 60% | 60% | 60% | 50% | 50% | 60% |
| HCT116 Human Colon Carcinoma | 85% | 70% | 70% | 80% | 85% | 55% | 80% | 65% |
| A549 Human Lung Carcinoma | 90% | 80% | 80% | 80% | 90% | 65% | 85% | 75% |
| MDA-MB-231 Human Breast Adenocarcinoma | 80% | 80% | 80% | 80% | 80% | 55% | 70% | 70% |
| MIAPaCa-2 Human Pancreatic Carcinoma | 70% | 60% | 65% | 65% | 70% | 70% | 60% | 80% |
| CIPAC-1 Human Pancreatic Adenocarcinoma | 55% | 55% | 55% | 65% | 55% | ND | 55% | ND |

REFERENCES

Agarwal et al., 1991. Pharmacokinetics, biodistribution, and stability of oligodeoxynucleotide phosphorothioates in mice. Proc. Natl. Acad. Sci. USA 88:7595–7599.

Agrawal, 1996. Antisense oligonucleotides: towards clinical trials, TIBTECH, 14:376.

Akhter et al, 1991. Interactions of antisense DNA oligonucleotide analogs with phospholipid membranes (liposomes). Nuc. Res. 19:5551–5559.

Amara et al., 1994. Phorbol ester modulation of a novel cytoplasmic protein binding activity at the 3'-untranslated region of mammalian ribonucleotide reductase R2 mRNA and role in message stability. J. Biol. Chem. 269:6709–7071.

Amara et al., 1995A. Altered regulation of message stability and tumor promoter-responsive cis-trans interactions of ribonucleotide reductase R1 and R2 messenger RNAs in hydroxyurea-resistant cells. Cancer Res. 55:4503–4506.

Amara et al., 1995B. Defining a novel cis element in the 3'-untranslated region of mammalian ribonucleotide reductase component R2 mRNA: Role in transforming growth factor-$_1$ induced mRNA stabilization. Nucleic Acids Res. 23:1461–1467.

Amara et al. 1996. Defining a novel cis-element in the 3'-untranslated region of mammalian ribonucleotide reductase component R2 mRNA: cis-trans interactions and message stability. J. Biol. Chem. 271:20126–20131.

Ashihara and Baserga, 1979. Cell Synchronization. Methods Enzymol. 58:248–262.

Blaesse, 1997. Gene Therapy for Cancer. Scientific American 276(6):111–115.

Björklund et al., 1993. Structure and promoter characterization of the gene encoding the large subunit (R1 Protein) of mouse ribonucleotide reductase. Proc. Natl. Acad. Sci. USA 90:11322–11326.

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).

Calabretta, et al, 1996. Antisense strategies in the treatment of leukemias. Semin. Oncol. 23:78.

Caceres and Kosik, 1990. Inhibition of neurite polarity by tau antisense oligonucleotides in primary cerebellar neurons. Nature, 343:461.

Capecchi, "Altering the genome by homologous recombination" *Science* 244:1288–1292 (1989).

Caras, 1985. Cloned Mouse Ribonucleotide Reductase Subunit M1 cDNA Reveals Amino Acid Sequence Homology with *Escherichia coli* and Herpesvirus Ribonucleotide Reductases. Biol. Chem. 260:7015–7022.

Chan et al., 1993. Phosphorylation of ribonucleotide reductase R2 protein: in vivo and in vitro evidence of a role for p34$^{cdc2}$ and CDK2 protein kinases. Biochemistry 32:12835–12840.

Chen et al., 1993. Mammalian ribonucleotide reductase R1 mRNA stability under normal and phorbol ester stimulating conditions: involvement of a cis-trans interaction at the 3'-untranslated region. EMBO J., 12:3977–3986.

Chen et al., 1994A. Regulation of mammalian ribonucleotide reductase R1 mRNA stability is mediated by a ribonucleotide reductase R1 mRNA 3'-untranslated region cis-trans interaction through a protein kinase C-controlled pathway. Biochem. J. 302:125–132.

Chen et al., 1994B. Defining a novel ribonucleotide reductase R1 mRNA cis element that binds to an unique cytoplasmic trans-acting protein. Nucleic Acids Res., 22:4796–4797.

Choy et al., 1988. Molecular mechanisms of drug resistance involving ribonucleotide reductase: hydroxyurea resistance in a series of clonally related mouse cell lines selected in the presence of increasing drug concentrations. Cancer Res. 48:2029–2035.

Cifone and Fidler, 1981. Increased metastatic potential is associated with increasing genetic instability of clones isolated from murine neoplasms. Proc. Natl. Acad. Sci. USA 78:6949–6952.

Crooke, 1995. Progress in antisense therapeutics, Hematol. Pathol. 2:59.

Damen et al., 1989. Generation of metastatic variants in populations of mutator and amplificator mutants. J. Natl. Cancer Inst. 81:628–631.

Davis et al., 1994. Purification, Characterization, and Localization of Subunit Interaction Area of Recombinant Mouse Ribonucleotide Reductase R1 Subunit. Biol. Chem. 269:23171–23176.

Davies et al., "Targeted alterations in yeast artificial chromosomes for inter-species gene transfer", *Nucleic Acids Research*, Vol. 20, No. 11, pp. 2693–2698 (1992).

Dickinson et al., "High frequency gene targeting using insertional vectors", *Human Molecular Genetics* Vol. 2, No. 8, pp. 1299–1302 (1993).

Duff and Lincoln, "Insertion of a pathogenic mutation into a yeast artificial chromosome containing the human APP gene and expression in ES cells", *Research Advances in Alzheimer's Disease and Related Disorders,* 1995.

Eckstein 1985. Nucleoside Phosphorothioates. Ann. Rev. Biochem. 54:367–402.

Egan, et al., 1987A. Expression of H-ras Correlates with Metastatic Potential: Evidence for Direct Regulation of the Metastatic Phenotype in 10T1/2 and NIH 3T3 Cells. Mol. Cell. Biol. 7:830–837.

Egan et al., 1987B. Transformation by oncogenes encoding protein kinases induces the metastatic phenotype. Science 238:202–205.

Eriksson et al., 1984. Cell cycle-dependent regulation of mammalian ribonucleotide reductase. The S phase-correlated increase in subunit M2 is regulated by de novo protein synthesis. J. Biol. Chem. 259:11695–11700.

Fan et al., 1996A. Ribonucleotide reductase R2 component is a novel malignancy determinant that cooperates with activated oncogenes to determine transformation and malignant potential. Proc. Natl. Acad. Sci. USA 93:14036–14040.

Fan et al., 1996B. A link between ferritin gene expression and ribonucleotide reductase R2 protein, as demonstrated by retroviral vector mediated stable expression of R2 cDNA. FEBS Lett. 382:145–148.

Fan et al., 1996C. Cloning of a gene from *Chlamydia trachomatis* that complements thymidylate synthase-deficient *Escherichia coli*. In: Abstracts of the 94th General Meeting of the American Society for Microbiology, p. 134.

Farrell and Lukens, 1995. Naturally occurring antisense transcripts are present in chick embryo chondrocytes simultaneously with the down-regulation of the α1 (I) collagen gene. J. Biol. Chem. 270:3400–3408.

Filatov et al., 1996. Induction of the mouse ribonucleotide reductase R1 and R2 genes in response to DNA damage by UV light. J. Biol. Chem. 271:23698–23704.

Ford et al., 1997. The poly (A) tail inhibits the assembly of a 3'- to 5' exonuclease in an in vitro RNA stability system. Mol. Cell. Biol. 17:398–406.

Galileo et al., 1991. J. Cell. Biol., 112:1285.

Gewirtz, 1993. Oligodeoxynucleotide-based therapeutics for human leukemias, Stem Cells Dayt. 11:96.

Gilboa et al., 1986. Transfer and expression of cloned genes using retroviral vectors. BioTechniques 4(6):504–512.

Gordon, 1989. Transgenic Animals. Intl. Rev. Cytol. 115: 171–229.

Hake and Richer, 1997. Translation regulation of maternal mRNA. Biochim. Biophys. Acta 1332:M31–M38.

Hampel and Tritz, 1989. RNA Catalytic Properties of the Minimum (−) sTRSV Sequence. Biochemistry 28:4929–4933

Hanania, et al 1995. Recent advances in the application of gene therapy to human disease. Am. J. Med. 99:537.

Huston et al, 1991 "Protein engineering of single-chain Fv analogs and fusion proteins" in Methods in Enzymology (J J Langone, ed.; Academic Press, New York, N.Y.) 203:46–88.

Huang and Wright, 1994. Fibroblast growth factor mediated alterations in drug resistance, and evidence of gene amplification. Oncogene 9:491–499.

Huang et al., 1995A. Drug resistance and gene amplification potential regulated by transforming growth factor $\beta_1$ gene expression. Cancer Res. 55:1758–1762.

Huang et al., 1995B. Multiple effects on drug sensitivity, genome stability and malignant potential by combinations of H-as, c-myc and mutant p53 gene overexpression. Int. J. Oncol. 7:57–63.

Hurta, et al., 1991. Early induction of ribonucleotide reductase gene expression by transforming growth factor $\beta_1$ in malignant H-ras transformed cell lines. J. Biol. Chem. 266:24097–24100.

Hurta and Wright, 1992. Alterations in the activity and regulation of mammalian ribonucleotide reductase by chlorambucil, a DNA damaging agent. J. Biol. Chem. 267:7066–7071.

Hurta and Wright, 1995. Malignant transformation by H-ras results in aberrant regulation of ribonucleotide reductase gene expression by transforming growth factor-$\beta_1$. J. Cell. Biochem. 57:543–556.

Huxley et al., "The human HPRT gene on a yeast artificial chromosome is functional when transferred to mouse cells by cell fusion", *Genomics,* 9:742–750 (1991).

Iyer et al. 1990. J. Org. Chem. 55:4693–4699.

Jakobovits et al., "Germ-line transmission and expression of a human-derived yeast artificial chromosome", *Nature,* Vol. 362, pp. 255–261 (1993).

Jensen et al., 1994. Identification of genes expressed in premalignant breast disease by microscopy-directed cloning. Proc. Natl. Acad. Sci, USA. 91:9257–9261.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203: 88–99.

Kimelman and Kirschner, 1989. An antisense mRNA directs the covalent modification of the transcript encoding fibroblast growth factor in *Xenopus* oocytes. Cell 59:687–696.

Klausner and Hartford, 1989. Cis-trans models for post-transcriptional gene regulation. Science 246:870–872.

Lamb et al., "Introduction and expression of the 400 kilobase precursor amyloid protein gene in transgenic mice", *Nature Genetics*, Vol. 5, pp. 22–29 (1993).

Lavitrano et al, 1989. Cell 57:717–723

Lee et al., 1993. The *C. Elegans* heterochronic gene lin-4 encodes small RNAs with antisense complementarity to lin-14. Cell 75:843–854.

Lefebvre-d'Hellencourt et al, 1995. Immunomodulation by cytokine antisense oligonucleotides. Eur. Cytokine Netw. 6:7.

Lev-Lehman et al., 1997. Antisense Oligomers in vitro and in vivo. In *Antisense Therapeutics*, A. Cohen and S. Smicek, eds (Plenum Press, New York)

Lewis et al., 1978. Assay of ribonucleotide reduction in nucleotide-permeable hamster cells. J. Cell Physiol. 94:287–298.

Lo, 1983. Mol. Cell. Biol. 3:1803–1814

Loke et al, 1989. Characterization of oligonucleotide transport into living cells. PNAS USA 86:3474.

Mann et al., 1988. Ribonucleotide reductase M1 subunit in cellular proliferation, quiescence, and differentiation. Cancer Res. 48:5151–5156.

Marzluff and Pandey, 1988. Multiple regulatory steps control histone mRNA concentrations. Trends Biochem. Sci. 13:49–52.

McClarty et al., 1990. Increased ferritin gene expression is associated with increased ribonucleotide reductase gene expression and the establishment of hydroxyurea resistance in mammalian cells. J. Biol. Chem. 265:7539–7547.

Miller et al., 1993. Use of retroviral vectors for gene transfer and expression. Meth. Enzymol. 217:581–599.

Mernaugh and Mernaugh, 1995 "An overview of phage-displayed recombinant antibodies" in Molecular Methods In Plant Pathology (RP Singh and US Singh, eds.; CRC Press Inc., Boca Raton, Fla.) pp. 359–365.

Morrison, 1991. Suppression of basic fibroblast growth factor expression by antisense oligonucleotides inhibits the growth of transformed human astrocytes. J. Biol. Chem. 266:728.

Nowell, 1986. Mechanisms of tumor progression. Cancer Res. 46:2203–2207.

Pearson and Choi, 1993. Expression of the human β-amyloid precursor protein gene from a yeast artificial chromosome in transgenic mice. Proc. Natl. Scad. Sci. USA 90:10578–82.

Qian et al, 1993. Cloning of a cDNA encoding an RNA binding protein by screening expression libraries using a Northwestern strategy. Biochemistry 212:547–554.

Radhakrishnan et al., 1990. The automated synthesis of sulfur-containing oligodeoxyribonucleotides using 3H-1, 2-Benzodithiol-3-One 1,1 Dioxide as a sulfur-transfer reagent. J. Org. Chem. 55:4693–4699.

Rastinejad et al. 1993. Tumor suppression by RNA from the 3' untranslated region of -tropomyosin. Cell 75:1107–1117.

Reichard, 1993. From RNA to DNA, why so many ribonucleotide reductases? Science 60:1773–1777.

Ross, 1995. mRNA stability in mammalian cells. Microbiol. Rev. 59:423–450.

Rosolen et al., 1990. Cancer Res. 50:6316.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rowley, 1990. Cytogenetics: Rosetta Stone for understanding cancer. Cancer Res. 50:3816–3825.

Sachs, 1993. Messenger RNA degradation in eukaryotes. Cell 74:413–421.

Saeki et al., 1995. Immunohistochemical detection of ribonucleotide reductase in human breast tumors. Int. J. Oncol. 6:523–529.

Scanlon et al., 1995. Oligonucleotides-mediated modulation of mammalian gene expression. FASEB J. 9:1288.

Schedl et al., "A yeast artificial chromosome covering the tyrosinase gene confers copy number-dependent expression in transgenic mice", *Nature*, Vol. 362, pp. 258–261 (1993).

Schwarz, 1988. Loss of growth factor dependence and conversion of transforming growth factor-$_1$ inhibition to stimulation in metastatic H-ras transformed murine fibroblasts. Cancer Res. 48:6999–7003.

Shaw et al., 1991. Modified deoxyoligonucleotides stable to exonuclease degradation in serum. Nucleic Acids Res. 19:747–750.

Spearman et al., 1994. Antisense oligodeoxyribonucleotide inhibition of TGF-$\beta_1$ gene expression and alterations in the growth and malignant properties of mouse fibrosarcoma cells. Gene 149:25–29.

Spitzer and Eckstein 1988. Inhibition of deoxynucleases by phosphorothioate groups in oligodeoxyribonucleotides. Nucleic Acids Res. 18:11691–11704.

Stokoe et al., 1994. Activation of Raf as a result of recruitment to the plasma membrane. Science 264:1463–1467.

Strauss et al., "Germ line transmission of a yeast artificial chromosome spanning the murine $\alpha_1$ (I) collagen locus", *Science*, Vol. 259, pp. 1904–1907 (1993).

Stubbe, 1989. Protein radical involvement in biological catalysis? Annu. Rev. Biochem. 58:257–285.

Taylor et al., 1992. Evidence for synergistic interactions between ras, myc and a mutant form of p53 in cellular transformation and tumor dissemination. Oncogene 7:1383–1390.

Thelander et al., 1985. Subunit M2 of mammalian ribonucleotide reductase. Characterization of a homogeneous protein isolated from M2-overproducing mouse cells. J. Biol. Chem. 260:2737–2741.

Thelander et al., 1980. Ribonucleotide reductase from calf thymus. Separation of the enzyme into two nonidentical subunits, proteins M1 and M2. J. Biol. Chem. 255: 7426–7432.

Thompson et al, 1989. Cell 56:313–321

Tlsty, 1990. Normal diploid human and rodent cells lack a detectable frequency of gene amplification. Proc. Natl. Acad. Sci. USA 87:3132–3136.

Tonin et al., 1987. Chromosomal assignment of amplified genes in hydroxyurea resistant hamster cells. Cytogenet. Cell Genet. 45:102–108.

Uhlenbeck, 1987. Nature 328:596–600

Van der Putten et al, 1985. PNAS USA 82:6148–6152

Wagner et al., 1996. Potent and selective inhibition of gene expression by an antisense heptanucleotide. Nature Biotechnology 14:840–844.

Wagner, 1994. Gene inhibition using antisense oligodeoxynucleotides. Nature 372:333.

Weber, 1983. Biochemical strategy of cancer cells and the design of chemotherapy. Cancer Res. 43:3466–3492.

Whitesell et al., 1991. Episome-generated N-myc antisense RNA restricts the differentiation potential of primitive neuroectodermal cell lines. Mol. Cell. Biol. 11:1360.

Wolman, 1983. Karyotypic progression in human tumors. Cancer Metastasis Rev. 2:257–293.

Woolf et al., 1990. The stability, toxicity and effectiveness of unmodified and phosphorothioate antisense oligodeoxynucleotides in *Xenopus* oocytes and embryos. Nucleic Acids Res. 18:1763–1769.

Wright et al., 1987. Altered Expression of Ribonucleotide Reductase and Role of M2 Gene Amplification in Hydroxyurea-Resistant Hamster, Mouse, Rat, and Human Cell Lines. Somat. Cell Mol. Genet. 13:155–165.

Wright, 1989A. Altered mammalian ribonucleotide reductase from mutant cell lines. Encycl. Pharmacol. Therapeut. 128:89–111.

Wright et al., 1989B. Hydroxyurea and related compounds. In: R. S. Gupta (ed.), Drug Resistance in Mammalian Cells, Boca Raton, Fla.; CRC Press, Inc; 15–27.

Wright et al., 1990A. Regulation and drug resistance mechanisms of mammalian ribonucleotide reductase and the significance to DNA synthesis. Biochem. Cell Biol. 68:1364–1371.

Wright et al., 1990B. DNA amplification is rare in normal human cells. Proc. Natl. Acad. Sci. USA. 87:1791–1795.

Wright et al., 1993. Transforming growth factor β and fibroblast growth factor as promoters of tumor progression to malignancy. Crit. Rev. Oncogen. 4:473–492.

Wright & Anazodo, 1995. Antisense Molecules and Their Potential For The Treatment Of Cancer and AIDS. Cancer J. 8:185–189.

Yakubov et al, 1989. PNAS USA 86:6454–6458.

DETAILED DESCRIPTION OF THE FIGURES

FIG. 1 is a photograph of a gel showing the expression of recombinant 3' UTRs in vector-transfected RMP-6 cells (Example 1). Total cellular RNA pretreated with or without DNase-free RNase A was used for the reverse transcriptase-PCR. The 5' and 3' primers were directed towards the UTRs and the vector, respectively. RMP-VC (Lanes 2, 7, 12), RMPM1U (Lanes 3, 4, 8, 9), RMPM2U (Lanes 5,6) and RMPC 0.8 (Lanes 13,14) were derived from RMP-6 cells after transfection with the vector control, the vector containing the R1 3' UTR, the vector containing the R2 3' UTR, or a chlamydial sequence by calcium phosphate precipitation, respectively. eRMP-VC (Lane 12), eRMPM1U (Lanes 5,6) and eRMPM2U (Lanes 10,11) were obtained by electroporation of the plasmids into RMP-6 cells. The left lane (Lane 1) shows the migration of 100 bp ladder marker (Pharmacia), and the lowest band is 100 bp.

FIG. 2 is a graph showing the growth of subcutaneous tumors in syngeneic mice (Example 1). The data for each point ±SE represents the results obtained for five mice. The latency periods for RMP-VC (○), RMPM1U (□) and RMPM2U (Δ) tumor cells were 8, 9 and 10 days following injection. Examination of the slopes of the curves indicated that the tumor growth rate of RMP-VC cells was significantly greater than the rate for RMPM1U ($p<0.01$) or RMPM2U ($p<0.005$) cells, respectively.

We claim:

1. An oligonucleotide comprising a sequence corresponding to a sequence segment of at least twenty consecutive nucleotides of a 3' untranslated region of a ribonucleotide reductase R1 mRNA, said oligonucleotide comprising a nucleic acid sequence selected from SEQ ID NOs: 1, 44, 45, 46, 47, 48 and 49, wherein the oligonucleotide is substantially free of coding sequence of said mRNA, and wherein the oligonucleotide is nuclease resistant and inhibits neoplastic cell growth.

2. An oligonucleotide comprising a sequence corresponding to a sequence segment of at least twenty consecutive nucleotides of a 3' untranslated region of a ribonucleotide reductase R2 mRNA as shown in SEQ ID NO:2, wherein the oligonucleotide is substantially free of coding sequence of said mRNA, and wherein the oligonucleotide is nuclease resistant and inhibits neoplastic cell growth.

3. The oligonucleotide according to claim 2, wherein the oligonucleotide comprises a nucleic acid sequence selected from SEQ ID NO: 6, SEQ ID NO: 7, SEQ ID NO: 8, SEQ ID NO: 9, SEQ ID NO: 10, SEQ ID NO: 11 and SEQ ID NO: 12.

4. The oligonucleotide according to claim 2, wherein the oligonucleotide comprises a nucleic acid sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

5. A chimeric oligonucleotide comprising two chemically distinct regions linked together, wherein a first region comprises an oligonucleotide selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 and 49 and said first region is joined to a second region comprising at least one modified nucleotide to form the chimeric oligonucleotide.

6. A composition formulated for local administration to a disease site, said composition comprising an effective amount of at least one oligonucleotide according to claim 1, in admixture with a pharmaceutically physiologically acceptable carrier or diluent.

7. A composition formulated for local administration to a disease site, said composition comprising an effective amount of at least one oligonucleotide according to claim 2, in admixture with a pharmaceutically physiologically acceptable carrier or diluent.

8. A composition formulated for local administration to a disease site, said composition comprising an effective amount of the chimeric oligonucleotide according to claim 5, in admixture with a pharmaceutically physiologically acceptable carrier or diluent.

9. A method of inhibiting neoplastic cell growth in a human or mouse comprising the step of locally administering to said human or mouse at a disease site a growth-inhibiting amount of an oligonucleotide comprising a sequence corresponding to:
- a) a 3' untranslated region of a ribonucleotide reductase R1 mRNA as shown in SEQ ID NO: 1; or
- b) a sequence segment of at least twenty consecutive nucleotides of said mRNA, said sequence segment comprising a nucleic acid sequence selected from SEQ ID NOs: 44, 45, 46, 47, 48 and 49, under conditions wherein the tumorigenicity of the neoplastic cells in said human or mouse is inhibited, and wherein said oligonucleotide is substantially free of coding sequence of said mRNA.

10. A method of inhibiting the metastasis of neoplastic cells in a human or mouse, comprising the step of locally administering to said human or mouse at a disease site an effective amount of an oligonucleotide comprising a sequence corresponding to:
- a) a 3' untranslated region of a ribonucleotide reductase R2 mRNA as shown in SEQ ID NO:2; or
- b) a sequence segment of at least twenty consecutive nucleotides of said mRNA, under conditions wherein the metastasis of the neoplastic cells in said human or mouse is inhibited, and wherein said oligonucleotide is substantially free of coding sequence of said mRNA.

11. The oligonucleotide according to claim 1, wherein the oligonucleotide comprises SEQ ID NO: 45.

12. The composition according to claim 6, wherein said oligonucleotide comprises SEQ ID NO: 45.

13. The composition according to claim 7, wherein said oligonucleotide comprises a nucleic acid sequence selected from SEQ ID NO: 6, SEQ ID NO: 7, SEQ ID NO: 8, SEQ ID NO: 9, SEQ ID NO: 10, SEQ ID NO: 11 and SEQ ID NO: 12.

14. The composition according to claim 7, wherein said oligonucleotide comprises a nucleic acid sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

15. The oligonucleotide according to claim 1, wherein said oligonucleotide comprises at least one modified base selected from the group consisting of xanthine, hypoxanthine, 2-aminoadenine, 6-methyl adenine, 2-propyl adenine, 5-halo-uracil, 5-halo-cytosine, 6-aza uracil, 6-aza cytosine and 6-aza thymine, pseudo uracil, 4-thiouracil, 8-halo adenine, 8-aminoadenine, 8-thiol adenine, 8-hydroxyl adenine, 8-halo guanine, 8-amino guanine, 8-thiol guanine, 8-hydroxyl guanine, 5-trifluoromethyl uracil and 5-trifluoro cytosine.

16. The oligonucleotide according to claim 1, wherein said oligonucleotide comprises one or more phosphorothioate, phosphotriester, methyl phosphonate, or phosphorodithioate internucleotide linkages.

17. The oligonucleotide according to claim 1, wherein said oligonucleotide is a peptide nucleic acid.

18. The oligonucleotide according to claim 1, wherein said oligonucleotide comprises a morpholino backbone structure.

19. The oligonucleotide according to claim 2, wherein said oligonucleotide comprises at least one modified base selected from the group consisting of xanthine, hypoxanthine, 2-aminoadenine, 6-methyl adenine, 2-propyl adenine, 5-halo-uracil, 5-halo-cytosine, 6-aza uracil, 6-aza cytosine and 6-aza thymine, pseudo uracil, 4-thiouracil, 8-halo adenine, 8-aminoadenine, 8-thiol adenine, 8-hydroxyl adenine, 8-halo guanine, 8-amino guanine, 8-thiol guanine, 8-hydroxyl guanine, 5-trifluoromethyl uracil and 5-trifluoro cytosine.

20. The oligonucleotide according to claim 2, wherein said oligonucleotide comprises one or more phosphorothioate, phosphotriester, methyl phosphonate, or phosphorodithioate internucleotide linkages.

21. The oligonucleotide according to claim 2, wherein said oligonucleotide is a peptide nucleic acid.

22. The oligonucleotide according to claim 2, wherein said oligonucleotide comprises a morpholino backbone structure.

23. The method according to claim 9, wherein the oligonucleotide comprises SEQ ID NO: 45.

24. A method of inhibiting neoplastic cell growth in a human or mouse comprising the step of locally administering to said human or mouse at a disease site a growth-inhibiting amount of an oligonucleotide comprising a sequence corresponding to:
- a) a 3' untranslated region of a ribonucleotide reductase R2 mRNA as shown in SEQ ID NO:2; or
- b) a sequence segment of at least twenty consecutive nucleotides of said mRNA, under conditions wherein the tumorigenicity of the neoplastic cells in said human or mouse is inhibited, and wherein said oligonucleotide is substantially free of coding sequence of said mRNA.

25. The method according to claim 24, wherein the oligonucleotide comprises a nucleic acid sequence selected from SEQ ID NOs: 6, 7, 8, 9, 10, 11 and 12.

26. The method according to claim 24, wherein the oligonucleotide comprises a nucleic acid sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

27. The method according to claim 24, wherein said neoplastic cells are selected from the group consisting of bladder, colon, lung, breast and pancreatic cancer cells.

28. The method according to claim 10, wherein the oligonucleotide comprises a nucleic acid sequence selected from SEQ ID NOs: 6, 7, 8, 9, 10, 11 and 12.

29. The method according to claim 10, wherein the oligonucleotide comprises a nucleic acid sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

30. The method according to claim 9, wherein said neoplastic cells are selected from the group consisting of bladder, colon, lung, breast and pancreatic cancer cells.

31. The method according to claim 10, wherein said neoplastic cells are selected from the group consisting of bladder, colon, lung, breast and pancreatic cancer cells.

32. A chimeric oligonucleotide comprising two chemically distinct regions linked together, wherein each of said regions comprises an oligonucleotide with a nucleic acid sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 and 49, joined to form the chimeric oligonucleotide.

33. A composition formulated for local administration to a disease site, said composition comprising an effective amount of the chimeric oligonucleotide according to claim 32, in admixture with a pharmaceutically physiologically acceptable carrier or diluent.

34. The method according to claim 9, wherein said neoplastic cells are derived from a cancer selected from the group of: leukemia, Hodgkins lymphoma, non-Hodgkins lymphoma, sarcoma, melanoma, adenoma, carcinoma of solid tissue, hypoxic tumor, genitourinary cancer, hematopoietic cancer, colon cancer, breast cancer, pancreatic cancer, head and neck cancer, and nervous system cancer.

35. The method according to claim 34, wherein said genitourinary cancer is cervical cancer or bladder cancer.

36. The method according to claim 34, wherein said carcinoma is a squamous cell carcinoma of the mouth, throat, larynx or lung.

37. The method according to claim 10, wherein said neoplastic cells are derived from a cancer selected from the group of: leukemia, Hodgkins lymphoma, non-Hodgkins lymphoma, sarcoma, melanoma, adenoma, carcinoma of solid tissue, hypoxic tumor, genitourinary cancer, hematopoietic cancer, colon cancer, breast cancer, pancreatic cancer, head and neck cancer, and nervous system cancer.

38. The method according to claim 37, wherein said genitourinary cancer is cervical cancer or bladder cancer.

39. The method according to claim 37, wherein said carcinoma is a squamous cell carcinoma of the mouth, throat, larynx or lung.

40. The method according to claim 24, wherein said neoplastic cells are derived from a cancer selected from the group of: leukemia, Hodgkins lymphoma, non-Hodgkins lymphoma, sarcoma, melanoma, adenoma, carcinoma of solid tissue, hypoxic tumor, genitourinary cancer, hematopoietic cancer, colon cancer, breast cancer, pancreatic cancer, head and neck cancer, and nervous system cancer.

41. The method according to claim 40, wherein said genitourinary cancer is cervical cancer or bladder cancer.

42. The method according to claim 40, wherein said carcinoma is a squamous cell carcinoma of the mouth, throat, larynx or lung.

43. A method of inhibiting neoplastic cell growth in a human or mouse comprising the step of locally administering to neoplastic cells an effective amount of an adenoviral vector comprising a nucleic acid sequence corresponding to:
    a) a 3' untranslated region of a ribonucleotide reductase R1 mRNA as shown in SEQ ID NO: 1; or
    b) a sequence segment of at least twenty consecutive nucleotides of said mRNA, said sequence segment comprising a sequence selected from SEQ ID NOs: 44, 45, 46, 47, 48 and 49,
    wherein said nucleic acid sequence is operatively linked to an expression control sequence and is substantially free of coding sequence of said mRNA, and wherein said nucleic acid sequence inhibits neoplastic cell growth.

44. The method according to claim 43, wherein said nucleic acid comprises SEQ ID NO: 45.

45. A method of inhibiting neoplastic cell growth in a human or mouse comprising the step of locally administering to neoplastic cells an effective amount of an adenoviral vector comprising a nucleic acid sequence corresponding to:
    a) a 3' untranslated region of a ribonucleotide reductase R2 mRNA as shown in SEQ ID NO: 2; or
    b) a sequence segment of at least twenty consecutive nucleotides of said mRNA,
    wherein said nucleic acid sequence is operatively linked to an expression control sequence and is substantially free of coding sequence of said mRNA, and wherein said nucleic acid sequence inhibits neoplastic cell growth.

46. The method according to claim 45, wherein said nucleic acid sequence comprises a sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

47. The method according to claim 45, wherein said nucleic acid sequence comprises a sequence selected from SEQ ID NOs: 6, 7, 8, 9, 10, 11 and 12.

48. A method of inhibiting the metastasis of neoplastic cells in a human or mouse comprising the step of locally administering to said neoplastic cells an effective amount of an adenoviral vector comprising a nucleic acid sequence corresponding to:
    a) a 3' untranslated region of a ribonucleotide reductase R2 mRNA as shown in SEQ ID NO: 2; or
    b) a sequence segment of at least twenty consecutive nucleotides of said mRNA,
    wherein said nucleic acid sequence is operatively linked to an expression control sequence and is substantially free of coding sequence of said mRNA, and wherein said nucleic acid sequence inhibits metastasis of neoplastic cells.

49. The method according to claim 48, wherein said nucleic acid sequence comprises a sequence selected from SEQ ID NOs: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 and 43.

50. The method according to claim 48, wherein said nucleic acid sequence comprises a sequence selected from SEQ ID NOs: 6, 7, 8, 9, 10, 11 and 12.

51. An adenoviral vector comprising the oligonucleotide according to claim 1 operatively linked to an expression control sequence.

52. An adenoviral vector comprising the oligonucleotide according to claim 2 operatively linked to an expression control sequence.

* * * * *